(12) United States Patent
Shin et al.

(10) Patent No.: US 9,655,916 B2
(45) Date of Patent: May 23, 2017

(54) COMPOSITIONS FOR EXTERNAL APPLICATION, CONTAINING ADENOSYLCOBALAMIN FOR IMPROVEMENT OF SKIN DISEASES

(71) Applicants: KOREA RESEARCH INSTITUTE OF CHEMICAL TECHNOLOGY, Daejeon (KR); HANALL BIOPHARMA CO., LTD., Daejeon (KR)

(72) Inventors: Byung Cheol Shin, Daejeon (KR); Hasoo Seong, Daejeon (KR); Aeri Lee, Incheon (KR); Jae Yang Kong, Daejeon (KR); Hyae Gyeong Cheon, Daejeon (KR); Young Sik Cho, Daejeon (KR); Sung Soo Jun, Seongnami-si (KR); Young Gwan Jo, Daejeon (KR)

(73) Assignees: KOREA RESEARCH INSTITUTE OF CHEMICAL TECHNOLOGY, Daejeon (KR); HANALL BIOPHARMA CO., LTD., Daejeon (KR)

( * ) Notice: Subject to any disclaimer, the term of this patent is extended or adjusted under 35 U.S.C. 154(b) by 184 days.

(21) Appl. No.: 14/600,253

(22) Filed: Jan. 20, 2015

(65) Prior Publication Data
US 2015/0196581 A1    Jul. 16, 2015

Related U.S. Application Data

(63) Continuation of application No. 13/679,029, filed on Nov. 16, 2012, now abandoned, which is a continuation-in-part of application No. 13/016,682, filed on Jan. 28, 2011, now abandoned, which is a continuation of application No. 11/996,574, filed as application No. PCT/KR2006/004233 on Oct. 18, 2006, now abandoned.

(30) Foreign Application Priority Data

Dec. 9, 2005 (KR) .......................... 10-2005-0120648

(51) Int. Cl.
| A61K 31/714 | (2006.01) |
| A61K 9/127 | (2006.01) |
| A61K 9/00 | (2006.01) |
| A61K 45/06 | (2006.01) |
| A61K 31/575 | (2006.01) |
| A61K 31/683 | (2006.01) |
| A61K 9/06 | (2006.01) |
| A61K 9/70 | (2006.01) |

(52) U.S. Cl.
CPC .......... *A61K 31/714* (2013.01); *A61K 9/0014* (2013.01); *A61K 9/127* (2013.01); *A61K 31/575* (2013.01); *A61K 31/683* (2013.01); *A61K 45/06* (2013.01); *A61K 9/06* (2013.01); *A61K 9/7053* (2013.01)

(58) Field of Classification Search
None
See application file for complete search history.

(56) References Cited

U.S. PATENT DOCUMENTS

| 5,798,341 A | 8/1998 | Klingelholler |
| 5,814,343 A | 9/1998 | Jones et al. |
| 6,255,294 B1 | 7/2001 | Armstrong et al. |
| 2002/0172710 A1 | 11/2002 | Twine |
| 2004/0170702 A1 | 9/2004 | VanStockum |

FOREIGN PATENT DOCUMENTS

| EP | 0 220 030 A2 | 4/1987 |
| EP | 0 256 472 A2 | 2/1988 |
| EP | 0 220 030 B1 | 6/1991 |
| JP | 2002-234845 A | 8/2002 |
| WO | 99/11242 A1 | 3/1999 |
| WO | 03/057192 A1 | 7/2003 |

OTHER PUBLICATIONS

International Searching Authority, International Search Report for PCT/KR2006/004233.
Stucker et al., "Topical vitamin B12—a new therapeutic approach in atopic dermatitis—evaluation of efficacy and tolerability in a random zed placebo controlled multicentre cliniml trial," British Journal of Dermatology, 2004, vol. 150, pp. 977-983.

*Primary Examiner* — Eric Olson
(74) *Attorney, Agent, or Firm* — Sughrue Mion, PLLC

(57) ABSTRACT

The present invention relates to a composition for external application for improving a skin disease (e.g. psoriasis). The composition contains adenosylcobalamin (coenzyme B12), optionally in admixture with other cobalamins. The composition can be present in the form of liposomal preparations, which are made of a phospholipid and cholesterol.

13 Claims, 5 Drawing Sheets

H&E Staining (X100)

Group 1 : Normal
Group 2 : Negative control (DNCB only)
Group 3 : Methylcobalamin embedded in liposome/gel (0.7%)
Group 4 : Cyanocobalamin embedded in liposome/gel (0.7%)
Group 5 : Adenosylcobalamin embedded in liposome/gel (0.7%)

Group 1 : Normal control
Group 2 : Negative control (DNCB only)
Group 3 : Positive control (Protopic® 0.1%)
Group 4.: Empty liposome/gel
Group 5 : 0.7% Adenosylcobalamin/cream
Group 6 : 0.7% Adenosylcobalamin/gel
Group 7 : Mixture of 0.7% adenosylcobalamin and empty liposome/gel
Group 8 : 0.7% Adenosylcobalamin embedded in liposome/gel

COMPOSITIONS FOR EXTERNAL APPLICATION, CONTAINING ADENOSYLCOBALAMIN FOR IMPROVEMENT OF SKIN DISEASES

CROSS REFERENCE TO RELATED APPLICATION

This application is a continuation of U.S. patent application Ser. No. 13/679,029 filed Nov. 16, 2012, which is a continuation of U.S. patent application Ser. No. 11/996,574 filed Jan. 23, 2008 (abandoned), which application is a national stage entry application of PCT/KR2006/004233 filed on Oct. 18, 2006, which claims priority benefits from Korean Patent Application Number 10-2005-0120648 filed Dec. 9, 2005, the disclosures of which are hereby incorporated by reference in their entities.

TECHNICAL FIELD

The present invention relates to a composition for external application for improving a skin disease, and particularly to a composition comprising adenosylcobalamin (coenzyme B12) as an active ingredient, which constitutes a coenzyme of cobalamin in pinocytosis, thereby enabling the improvement of conventional preparation containing cobalamin and its derivative. And this shows delayed pharmaceutical action and is very low in bioavailability as more than 90% of cobalamin or its derivative relative is excreted relative to 100% of administered dosage due to its high molecular weight.

RELATED PRIOR ART

Dermatitis is an inflammation caused by various external or internal reasons, and is usually referred to as eczema and includes atopic dermatitis, contagious dermatitis and seborrheic dermatitis.

Although atopic dermatitis is known to be related to immunoglobulin (IgE), it is not certain up to the present of what causes atopic dermatitis. An atopic dermatitis displays symptoms due to external factors, such as various antigens, as it has over-sensitive atopic characteristic to specific substance. The region with the symptoms of atopic dermatitis is mainly focused on the face in infancy such as in the form of facial rubefaction, exudative inflammation and desquamation, as well as being very itch. Although the region with the symptoms is usually limited to face in infancy, the symptoms gradually spread to arms and legs, and develop papule pilaris (i.e. atopic skin). Although there are many cases where dermatitis is cured before 12 years old, adults with dermatitis have lichen symptoms on the face, breast and the back of the neck besides arms and legs. This may develop into childhood asthma, and it may take a long period of time until dermatitis may be completely cured. However, there are also many cases where dermatitis returns or relapses and is not completely cured.

An antihistaminic agent and steroid are currently used to treat dermatitis including atopic dermatitis. An antihistaminic agent is usually used to suppress itching, and some of the examples include promethamine hydrochloride, chlorophenylamine maleate, diphenhydramine hydrochloride and mequitazine. Steroid has various side effects despite its remarkable clinical efficacy, and some of the examples include hydrocortisone butyrate, dexametasone valerate, betametasone dipropionate, chlorobetasole propionate and prednisolone. Considering the therapeutical efficacy, the medicine for external application (e.g. ointments) is the most effective and there is no substitute known for this form of medicine. Furthermore, along with the therapeutical effect, the aforementioned medicines are known to have side effects, such as induced infection, secondary adrenocortical insufficiency, diabetes, peptic ulcer, hirsutism, alopecia and pigmentation, etc. In particular, the medicines for external application such as ointments show serious side effects such as skin thinning or shrinking and flushing due to direct influence of the medicine on the skin. Therefore, there is urgent need for stable medicine with less side effects than the conventional dermatitis medicines.

Cobalamin or vitamin B12 is soluble in aqueous solution with the complicate structure, which is one of vitamin B group found in foods. The basic chemical structure of cobalamin comprises two moieties, i.e. porphyrin cyclic structure and nucleotide with alpha-glycoside bonds. The porphyrin cylic structure include four 5,6-dimethylbenzimidazole rings, four nitrogen atoms of which form a coordinate covalent bond with cobalt ion to provide a chelate compound. Cyanocobalamin is a cobalamin where the cobalt atom is bound with cyano group, and the structure without this cyano group is important nutritionologically as well as biochemically. In other words, the cyano group is removed before the activation in a body, and cobalamin changes into co-enzyme and cobalamin enzyme.

Human cannot synthesize a porphyrin cyclic structure, and hence totally depends on foods for the vitamin B12. Although only microorganisms may synthesize a basic cobalamin molecule, cells of all the mammals can change cobalamin into coenzymes, i.e. adenosylcobalamin and methylcobalamin. Hydroxocobalamin, methylcobalamin and adenosylcobalamin are the three types of cobalamin that are separated from the mammal tissues most frequently. However, only methyl cobalamin and adenosylcobalamin may act as a supplemental factor in human enzyme. Adenosylcobalamin constitutes components in cells and exists in mitochondria, while methyl cobalamin is usually found either in body fluid such as serum and cerebral spinal fluids or in cytoplasm. Cobalamin and its derivatives are reported to have an activity of suppressing dermatitis, especially an inflammation of atopic eczema, which is known to be caused by the production of inflammatory cytokine such as interleukin (IL)-1 alpha, IL-2, IL-6 and interferon (IFN)-gamma [Yamashiki M., Nishimura A., Kosaka Y.; J. Clin. Lab. Immunol.; 1992; 37; 173-182]. Furthermore, cobalamin and its derivatives are the main cause for rubefaction and itching in atopic dermatitis, and are reported to effectively suppress the generation of NO, which is induced by inflammatory cytokine [Stucker M., Pieck C., Stoerb C., Niedner R., Hartung J., Altmeyer P.; Br. J. Dermatol.; 2004; 150; 977-983]. As described above, there have been attempts made to prepare medicine for external application based on the therapeutic effect of cobalamin and its derivatives against dermatitis.

However, the prior techniques that apply cobalamin and its derivatives for treating dermatitis, especially atopic dermatitis, failed in maximizing the effect partially, as follows. First, they mainly used cyanocobalamin derivatives as an active ingredient and could not maintain the effect until cyanocobalamin derivatives changed into adenosylcobalamin in the human body. Second, cobalamin is sensitive and unstable to light and heat, and the effect of the medicine could easily decrease. Third, the skin penetration rate is low with low treating effect.

To solve the aforementioned problems, there have been other attempts to prepare the external formulations such as liposome, cream or gel by using adenosylcobalamin as an active ingredient along with incorporation of skin accelerator to increase skin penetration rate of an active ingredient.

U.S. Pat. No. 5,798,341 (Aug. 25, 1998) discloses a method of using cyanocobalamin, hydroxocobalamin and methylcobalamin in preparing medicine for external application, while U.S. Pat. No. 6,255,294 (Jul. 3, 2001) of Allergy Limited discloses a method of delivering cobalamin and its derivatives by oral or parenteral route in forms of tablets, gum, sublingual and mucous formulations. On the other hand, U.S. patent application Ser. No. 10/782,827 (Sep. 2, 2004) of Audrey discloses a method of preparing tablets, injections, and preparations for skin application by using vitamin B12 in combination with copper, folic acid and vitamin C. And U.S. patent application Ser. No. 09/858, 038 (Nov. 21, 2002) discloses a method of formulating vitamin B12 into liposome, and administering the formulation to patients with special diseases. Furthermore, Adeptsrus Holding Company (Canada) has been attempting to develop a cream for functional cosmetics containing vitamin B12 to protect skin cells and maintain water retention within skin.

However, the formulations according to the aforementioned prior arts contain cyanocobalamin, hydroxocobalamin and methylcobalamin as an active ingredient, and fail to show prompt pharmaceutical effect as the cobalamin derivatives above need to be changed into adenosylcobalamin having coenzyme function for pharmaceutical effect through the metabolism in a body. Furthermore, the attempts to formulate cobalamin and its derivatives into oral preparations, injections and transdermal preparations were not successful for the following reasons: Cobalamin or its derivatives, when orally administered, show very low bioavailability. That is, more than 90% of orally administered cobalamin or its derivatives are excreted within 48 hours with regarding to injections, there has been no specific and detailed description about the techniques to embed cyanocobalamin into liposome and formulate the injections. In particular, only small amount of cobalamin or its derivatives remains in skin when injected, which requires a long-term injections to achieve desired results. Moreover, the technique has not been developed to increase the skin penetration rate of cobalamin and its derivatives, which, in turn, would increase the therapeutical effect.

Thus, the present inventors completed the present invention by employing a composition comprising adenosylcobalamin as an active ingredient, and formulating the composition into a form of emulsion creams, hydrated gels and gels comprising adenosylcobalamin containing liposome particles, along with incorporation of skin accelerator, thus enabling the increase in the therapeutic effect for dermatitis.

Therefore, the present invention aims to provide a composition for external application, which comprises adenosylcobalamin as an active ingredient, thus improving the effect of skin penetration.

DETAILED DESCRIPTION OF INVENTION

The present invention relates to a composition for external application for improving a skin disease, which comprises adenosylcobalamin as an active ingredient. The adenosylcobalamin may be loaded in liposome comprising phospholipid and cholesterol. Moreover, the composition herein may further comprise a surfactant with $C_8$-$C_{16}$ alkyl group to the aforementioned active ingredients.

Hereunder is provided a detailed description of the present invention.

The present invention relates to a composition comprising as an active ingredient adenosylcobalamin (coenzyme B12), which constitutes the coenzyme of cobalamin in pinocytosis, thereby enabling the improvement of the conventional preparation containing cobalamine and its derivative. And, this shows delayed pharmaceutical action and is very low in bioavailability as more than 90% of cobalamin or its derivative relative is excreted relative to 100% of administered dosage.

Cobalamin or its derivatives, which are currently used for treating dermatitis, have drawbacks of delayed pharmaceutical action and low treatment efficacy as they cannot show pharmaceutical action until they are transformed into coenzyme and their skin permeation rate is low, respectively. On the other hand, adenosylcobalamin, which is used as an active ingredient in the present invention, may exert a pharmaceutical action as a coenzyme without a metabolism process in the body, thus resulting in prompt pharmaceutical action. Moreover, the composition herein comprises biologically friendly skin accelerator, thus improving the skin permeation of the active ingredients and is superior in treating atopic dermatitis, eczema and psoriasis.

Hereunder is provided a detailed description of a method for preparing adenosylcobalamin containing liposome according to the present invention.

The Liposome particles were prepared by adding saccharides into conventionally obtained liposome, followed by freeze drying.

First of all, at least one phospholipid was selected among phosphocholine based compounds (PC), and was hydrated by mixing with at least one selected from phospholipids and cholesterol, followed by freeze drying, to provide liposome particles.

The phospholipids and cholesterol were admixed in a mixing ratio of 1-10:1 (w/v). The aforementioned cholesterol is used to enhance the hydrophobic binding, and there may be aggregation or agglomeration between the liposome particles when the mixing ratio is outside the aforementioned range. Preferably, the concentration of the mixed phospholipid is controlled within 0.1-10 mM, and in case of being outside the aforementioned range, the embedding proportion of drugs may be lowered and the liposome particles may be aggregated or agglomerated, deteriorating the stability.

The phosphocholine based compound (PC) has 3-24 carbons in diacyl group, and preferably is at least one selected among 1,2-dipalmitoyl-sn-glycero-3-phosphocholine (DPPC), 1,2-disteroyl-sn-glycero-3-phosphocholine (DSPC), L-a-phosphatidylcholine (HSPC), 1-palmitoyl-2-glutaroyl-sn-glycero-3-phosphocholine (PGPC), 1,2-dilauroyl-sn-glycero-3-phosphocholine (DLPC), 1,2-dimyristoyl-sn-glycero-3-phosphocholine (DMPC) and 1,2-dioleyl-sn-glycero-3-phosphocholine (DOPC).

The aforementioned mixture is dissolved in a lipid-soluble solvent such as chloroform, methanol and ethanol, followed by removing the solvent with an evaporation condenser, thus providing a thin lipid layer. Ammonium sulfate solution, which may act in drug loading through the concentration difference, is added to hydrate the lipid layer, thus forming liposome. The formed liposome aforementioned is then extruded at a reduced pressure, thus providing liposome particles with a particle size of 30-400 nm, and preferably of 90-120 nm.

Adenosylcobalamin is loaded into the liposome by adding adenosylcobalamin. The non-loaded adenosylcobalamin is removed by dialysis. The loading efficiency is 70-100%.

Then, saccharide is added in thus-obtained liposome solution into the concentration of 0.01-80 mM (w/v) for 1-30 minutes followed by freeze drying, to provide liposome particles containing powdered adenosylcobalamin.

The aforementioned saccharides are monosaccharides, disaccharides or polysaccharides and not specifically limited to any type, yet some of the representative examples of the monosaccharide include mannitol, maltose, glucose, mannose and fructose, the examples of the disaccharide include maltose, sucrose and trehalose, and the examples of and the polysaccharide include sorbitol, dextrin and glucosamine. The aforementioned saccharide is dissolved in the distilled water, and the solution is prepared into the concentration of 0.01-80 mM. The concentration below 0.01 mM may deteriorate the stability of liposome in freeze-drying process and may induce aggregation or agglomeration of liposome particles, while the concentration above 80 mM would induce the increase of viscosity and cause the weakening of gel, as there is considerably larger quantity of saccharide included, in comparison to the phospholipids. The freeze drying process is divided into a freezing process at the temperature between −80° C. and −70° C. and a consecutive drying process at the temperature between −50° C. and −40° C.

As described above, the liposome particles containing adenosylcobalamin, prepared according to the present invention, serve as the supports for maintaining the liposome forms at re-dispersion. Due to the rapid dispersion of saccharides, adenosylcobalamin may be stored for a long period of time and improved its stability, with selective control of the optimal storage temperature, specific saccharides, the concentration and the mixing ratio of liposome.

Hereunder is provided a detailed description of a method for preparing hydrogel containing adenosylcobalamin according to the present invention.

First of all, the water-soluble base is completely dissolved in the distilled water in the concentration of 3-10 wt %, and adenosylcobalamin is added into the solution to provide a uniform aqueous solution. 0.5-2 wt % of emulsifying agent and 40-60 wt % of solvent are also added to the aforementioned solution, and then the distilled water is further added to balance out the amount. The aforementioned mixture is stirred with a homomixer at 3,000-6,000 rpm until it becomes uniform, thus producing gel.

Some of the examples of the water-soluble base include but are not limited to carbopol, carbomer, polyethylene glycol, polypropylene glycol, polyacrylic acid, carboxymethyl cellulose, hydroxymethyl cellulose, polyvinylpyrrolidone, gelatine, alginate salt, chitin, or chitosan derivatives and their mixture. Moreover, although it is preferred to use non-ionic surfactant as the emulsifying agent, other materials may also be used without limitation for this purpose, such as polyoxyethylene fatty acid ester, polyoxyethylene glycerine fatty acid ester, polyoxyethylene sorbitan fatty acid ester, glyceryl fatty acid ester, or their mixture. Some of the examples of the solvent include but are not limited to ethanol, isopropanol, ethyl acetate, propylene glycol, ethoxydiglycol and their mixture.

Hereunder is provided a detailed description of a method for preparing emulsion cream containing adenosylcobalamin according to the present invention.

First of all, 0.1-2.0 wt % of sodium hydroxide is completely dissolved in the distilled water of third stage, and adenosylcobalamin is also added in this aqueous solution, followed by stirring at 60-90° C. with a magnetic stirrer until adenosylcobalamin is completely dissolved, thereby producing an aqueous phase containing an active ingredient. A base forming an oil phase and an emulsifying agent are added in a concentration of 5.0-15.0 wt % and 2.0-10.0 wt % relative to the total composition, followed by stirring at 60-90° C. with a magnetic stirrer until all the ingredients are completely dissolved, thereby producing an oil phase.

The aqueous phase and the oil phase are slowly admixed at 60-90° C. and stirred with a paddle mixer for 20 minutes, followed by stirring with a homomixer at 3,000-10,000 rpm until the composition becomes uniform, while being slowly cooled down to 20-40° C. with a constant temperature bath, thereby producing emulsified cream, and the produced foam is completely removed with vacuum.

The base forming an oil phase herein includes saturated or unsaturated hydrocarbon-based oil and a mixture thereof. Some of the examples of the aforementioned saturated hydrocarbon-based oil include but not limited to liquid paraffin, paraffin wax, squalene, vaseline and other branched chain hydrocarbon-based oil, while some of the examples of the aforementioned saturated or unsaturated hydrocarbon-based oil include but not limited to natural oils, such as animal fat and vegetable oil, all of which can be used in the present invention.

In particular, another feature of the present invention is that the composition for external application herein further comprises 50-500 weight parts of a skin permeation enhancer relative to one weight part of the active ingredients, hence increasing the therapeutical effect of the active ingredients.

The contents of the aforementioned skin permeation enhancer below 50 weight parts may not be sufficient to enhance the skin absorption of the active ingredients, while the content above 500 weight parts may cause phase separation of the preparation or diminish the feeling when applied on the skin.

Among surfactants with $C_8$-$C_{16}$ alkyl group, lauryl ether based compound or polyethylene oxide (PEO) based compound is added in preparing formulation as skin permeation enhancer, in order to increase the skin-absorption and the skin-affinity. Some of the representative examples of lauryl ether based compound include, without limitation, isopropyl myristate, Brij 30, sodium lauryl sulfate, propylene glycol monolaurate, monolaurin, monostearin, monoolein, monomyristin, lauryl alcohol or polyoxyethylene-9-lauryl ether. Some of the examples of the poly ethylene oxide based compound include, without limitation, Brij 90, pluronic, sorbitan monopalmitate and sorbitan trioleate.

As described above, the present inventors ascertained that the adenosylcobalamin containing composition for external application herein has superior effect of treating dermatitis in comparison to the conventional composition for treating skin diseases containing cobalamin or its derivatives. This adenosylcobalamin containing composition herein is preferred to comprise 0.01-7 wt % of the active ingredients relative to 100 wt % of total composition. The content of lower than 0.01 wt % may not show satisfactory therapeutical effect, while the content of higher than 7 wt % may cause skin irritation.

Moreover, the composition herein may further comprise at least one known component such as methylcobalamin, hydroxocobalamin and cyanocobalamin besides adenosylcobalamin, thus providing equivalent or superior effect.

Furthermore, the composition herein may further comprise steroid such as dexametasone, betametasone, hydrocortisone, prednisolone and clobetasol; immunosuppressive drug such as tacrolimus, Pimecrolimus and cyclosporine; and vitamin such as tretionin, vitamin E-acetate and vitamin B5, besides the active ingredients, thus showing increased effect.

Meanwhile, the composition herein may be formulated into either medicine in the form of ointment, solution, suspension, plaster and water-containing plaster or cosmetics in the form of emulsion, lotion, cream, pack, skin lotion and soap, by using the active ingredient and pharmaceutically acceptable carrier or excipient according to the conventional methods.

Although the effective application dosage of the aforementioned active ingredients depends on the severity or the region of dermatitis as well as the age of the patient, it may be applied, for example, twice or several times a day with a dosage of 0.1-5.0 g per each application.

EXAMPLES

Figure 1:
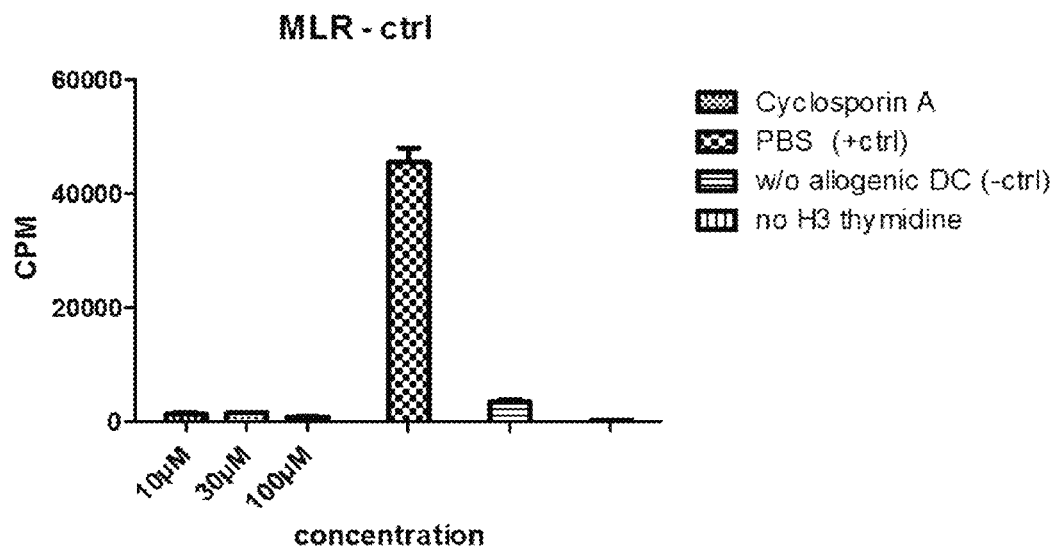
FIGS. 1 to 3 show the results of the experiments for MLR response of the Control group, Photo-nonexposed group, and Photo-exposed group, respectively.

The present invention is described more specifically by the following Examples. Examples herein are meant only to illustrate the present invention, but in no way to limit the claimed invention.

Example 1

Adenosylcobalamin containing liposome herein was prepared as described below under the condition that light is blocked.

1,2-distearoyl-sn-glycero-3-phosphocholine (DPPC) and cholesterol (CHOL) were dissolved in 5 mL of chloroform into the concentration of 9.58 mg/mL and 3.19 mg/mL, respectively, followed by vacuum distillation with a rotational evaporation condenser at a temperature above the phase transition temperature (41° C.), thus providing thin lipid membrane on the round flask wall. Chloroform remaining in a flask was completely removed through vacuum drying for 24 hours.

Hydration was performed by adding 10 mL of ammonium sulfate solution (250 mM) until the lipid membrane was completely dispersed, followed by stirring for 10 minutes at an interval of 2 minutes, thus providing multi-membrane liposome. After hydration, mono-membrane liposome particles were prepared by passing through a polycarbonate membrane with porosity of 200 nm (5 times) and a polycarbonate membrane with 100 nm (5 times) by using a pressurized extruder. Ammonium sulfate containing liposome was prepared by performing membrane dialysis with ammonium sulfate that is not comprised in liposome at 4° C. for 24 hours.

After adenosylcobalamin solution was prepared by dissolving adenosylcobalamin in 10% (w/v) sucrose aqueous solution into the concentration of 1.5 mg/mL, 10 mL of the solution was added in the aforementioned ammonium sulfate containing liposome, followed by stirring at 60° C. for 2 hours, and then membrane dialysis was performed with adenosylcobalamin that is not comprised in liposome at 4° C. for 48 hours, thus producing adenosylcobalamin containing liposome.

After maltose aqueous solution (30 mM) was prepared by using the distilled water of third stage, the solution was added in the same amount of the adenosylcobalamin containing liposome solution that was produced at 4° C., thus performing reaction, followed by freezing in a deep freezer at −77° C. for 12 hours and drying in a freeze-dryer at −45° C. for 24 hours for pulverization.

Example 2

Adenosylcobalamin containing gel herein was prepared as described below under the condition where light is blocked.

70.0 mg of adenosylcobalamin was exactly weighed as an active ingredient, and added into 30 mL of the distilled water of third stage, followed by gentle agitation with magnetic stirrer to dissolve adenosylcobalamin completely. 2.2 g of carbomer 940 was completely dissolved as a base under gentle agitation while being added in a small amount. 5.0 g of polyethylene glycol (PEG) 1000, 1.35 g of diethyl amine (DEA) and 55.0 mL of ethanol were added in the solution as a base, an emulsifying agent and a solvent, respectively. Third distilled water was added to provide 100 g of total solution, followed by agitation at room temperature and 3,000 rpm with homomixer until the solution becomes uniform, thus producing adenosylcobalamin containing gel.

Example 3

Adenosylcobalamin containing cream herein was prepared as described below under the condition that light is blocked.

1.0 g of sodium hydroxide was completely dissolved in 70 mL of the distilled water of third stage. 70.0 mg of adenosylcobalamin was exactly weighed as an active ingredient, and added into the sodium hydroxide aqueous solution, followed by stirring with a magnetic stirrer at 90° C. until adenosylcobalamin is completely dissolved, thus producing an aqueous phase containing an active ingredient. 13 g of stearic acid (a base) and 4 g of lanolin, 2 g of sucrose fatty acid ester (an emulsifying agent) were completely dissolved with 2 g of isopropyl myristate at 90° C. with a magnetic stirrer, thus producing an oil phase.

The aqueous phase and the oil phase obtained pursuant to above were slowly admixed at 90° C. and stirred with a paddle mixer for 20 minutes, followed by stirring with a homomixer at 3,000 rpm until the solution becomes uniform, while being slowly cooled down to 40° C. with a constant temperature bath, thus producing emulsified cream, and the produced foam was completely removed with vacuum.

Example 4

Gel containing the adenosylcobalamin containing liposome herein was prepared as described below under the condition that light is blocked.

The experiment was performed by following the same procedure as in Example 2, except by using 100 mg of powdered adenosylcobalamin containing liposome that was prepared in Example 1 as an active ingredient, instead of adenosylcobalamin.

Comparative Example 1

Liposome was prepared by following the same procedure as in the Example 1 except the use of cyanocobalamin instead of adenosylcobalamin as an active ingredient.

Comparative Example 2

Gel was prepared by following the same procedure as in the Example 2 except the use of cyanocobalamin instead of adenosylcobalamin as an active ingredient.

Comparative Example 3

Cream was prepared by following the same procedure as in the Example 3 except the use of cyanocobalamin instead of adenosylcobalamin as an active ingredient.

Comparative Example 4

Gel was prepared by following the same procedure as in the Example 4 except the use of powdered cyanocobalamin (100 mg) instead of adenosylcobalamin as an active ingredient.

Example 5

Gel was prepared by following the same procedure as in Example 2 except the addition of Lutrol 75 (1.0 g) as skin accelerator, together with adenosylcobalamin.

Example 6

Cream was prepared by following the same procedure as in Example 3 except the addition of Brij 30 (1.5 g) as skin accelerator together with adenosylcobalamin.

Example 7

Gel was prepared by following the same procedure as in Example 4 except the addition of sorbitan trioleate (1.7 g) as skin accelerator together with adenosylcobalamin.

Example 8

Gel was prepared by following the same procedure as in Example 5 except the addition of adenosylcobalamin (70 mg) and methyl cobalamin (30 mg).

Example 9

Cream was prepared by following the same procedure as in Example 6 except the addition of adenosylcobalamin (70 mg) and dexametason propionate (50 mg).

Example 10

Cream was prepared by following the same procedure as in Example 6 except the addition of adenosylcobalamin (70 mg) and tacrolimus hydrate (15 mg).

Example 11

Cream was prepared by following the same procedure as in Example 6 except the addition of adenosylcobalamin (70 mg) and tretionin (25 mg).

Test Example 1: Evaluation of Medicine for External Application in Anti-Inflammatory Activity Hereunder is provided a description of how to evaluate the activity in treating dermatitis of the adenosylcobalamin containing preparations prepared in Examples 2-4, the cyanocobalamin containing preparations prepared in Comparative Examples 2-4, preparations further containing skin accelerator preparations prepared in Examples 5-7 and preparations containing multi-components prepared in Examples 8-11.

The animal test subjects with dermatitis were prepared as follows, and the activity of suppressing edema and rubefaction was evaluated. Moreover, a base control without an active ingredient was also prepared by adding base components. Positive control medicine was prepared by 0.1% tacrolimus ointment and 0.1% dexametasone cream.

Preparation of Animal Test Subject with Dermatitis 7-week-old female BALB/C mice were used as test subjects. Ovalbumin and aluminium hydroxide gel was suspended in physiological saline solution into final concentration values of 2 mcg/mL and 100 mg/mL. On the first test day, 0.5 mL of each suspension was administered to the abdomen of the mice, and 0.5 mL of each suspension was further administered on the $14^{th}$ day. On the $28^{th}$ day, 25 mL of ovalbumin (concentration: 20 mcg/mL) was subcutaneously administered to the right external ear of the mice to induce edema. 24 hours after the edema induction, rubefaction was ascertained to take place.

Measurement of Activity of Suppressing Edema

Base control, test preparations and positive control were applied to the external ear, i.e. edema induced area, 1 hour and 4 hours after edema induction in a dosage of 100 μL per skin area 10 cm$^2$. The thickness of external ear was measured by using a dial thickness gauge. The increase in external ear thickness was calculated by deducting the value of external ear thickness before edema induction from the value of external ear thickness after edema induction. Suppression was obtained by using the following mathematical formula and the results were provided in Table 1.

Mathematical formula $$\text{Rate of suppression}(\%) = \frac{\text{Thickness increase(Control group)} - \text{Thickness increase(Experimental group)}}{\text{Thickness increase(Control group)} - \text{Thickness increase(Non-induced group)}} \times 100$$

TABLE 1

| Preparations | No. of subjects | Suppression (%) after 4 hrs | Suppression (%) after 24 hrs | Suppression (%) after 48 hrs |
|---|---|---|---|---|
| Control | 3 | 0 | 0 | 0 |
| Positive control (0.1% tacrolimus ointment) | 5 | 45.0 | 75.2 | 100.0 |

TABLE 1-continued

| Preparations | No. of subjects | Suppression (%) after 4 hrs | Suppression (%) after 24 hrs | Suppression (%) after 48 hrs |
|---|---|---|---|---|
| positive control (0.1% dexametasone cream) | 5 | 38.4 | 62.7 | 93.1 |
| Example 2 | 5 | 27.4 | 50.5 | 67.2 |
| Example 3 | 5 | 28.2 | 49.1 | 71.6 |
| Example 4 | 5 | 23.6 | 38.6 | 60.2 |
| Comp. Ex. 2 | 5 | 19.5 | 36.7 | 45.4 |
| Comp. Ex. 3 | 5 | 15.1 | 32.5 | 48.8 |
| Comp. Ex. 4 | 5 | 13.3 | 30.8 | 42.3 |
| Example 5 | 5 | 43.7 | 61.4 | 88.3 |
| Example 6 | 5 | 47.2 | 66.7 | 90.6 |
| Example 7 | 5 | 37.5 | 58.1 | 78.4 |
| Example 8 | 5 | 46.3 | 70.6 | 94.5 |
| Example 9 | 5 | 50.2 | 82.3 | 100.0 |
| Example 10 | 5 | 49.6 | 81.7 | 100.0 |
| Example 11 | 5 | 38.2 | 65.6 | 89.2 |

As set forth in Table 1, the adenosylcobalamin containing preparations of Examples 2-4 were superior to the cyanocobalamin containing preparations of Comparative Examples 2-4 in suppressing edema. Preparations further containing skin accelerator in Examples 5-7 showed more superior activity compared to the preparations of Examples 2-4. Multi-component preparations in Examples 8-11 were also superior to single-component preparations in Examples 5-7.

Evaluation of Activity of Suppressing Edema

Base control, test preparations and positive control were applied to the external ear, i.e. edema induced area, 2 and 4 hours after edema induction in a dosage of 100 μL per skin area 10 cm². The thickness of external ear was measured with the unaided eye. The degree of rubefaction was evaluated with numerical values as follows: zero for a subject with no rubefaction, one for a subject with dark or light reddish small-sized rubefaction, three for a subject with dark reddish large-sized rubefaction, with two for a subject with rubefaction with the degree of the rebufaction value between three and one, and the results were provided in Table 2.

TABLE 2

| Preparations | No. of subjects | Degree of rubefaction after 4 hrs | Degree of rubefaction after 24 hrs |
|---|---|---|---|
| Base control | 3 | 0.9 ± 0.1 | 2.6 ± 0.1 |
| Positive control (0.1% tacrolimus ointment) | 5 | 0.5 ± 0.1 | 1.1 ± 0.2 |
| Positive control (0.1% dexametasone cream) | 5 | 0.5 ± 0.2 | 1.2 ± 0.1 |
| Example 2 | 5 | 0.6 ± 0.2 | 1.4 ± 0.1 |
| Comp. Ex. 2 | 5 | 0.8 ± 0.2 | 1.8 ± 0.1 |
| Example 5 | 5 | 0.5 ± 0.2 | 1.3 ± 0.2 |
| Example 8 | 5 | 0.5 ± 0.1 | 1.1 ± 0.1 |
| Example 10 | 5 | 0.4 ± 0.2 | 0.9 ± 0.1 |

As set forth in Table 2, the adenosylcobalamin containing preparations of Example 2 were superior to the cyanocobalamin containing preparations of Comparative Example 2 in suppressing rubefaction. Preparations further containing skin accelerator in Example 5 showed superior activity compared to the preparations of Example 2. Multi-component preparations in Example 8 and Example 10 were also more superior to single-component preparations in Example 2.

Test Example 2: Evaluation in Skin Water Retention

Hereunder is provided a description of how to evaluate the skin water retention of the adenosylcobalamin containing preparations prepared in Example 2, the cyanocobalamin containing preparations prepared in Comparative Example 2, the adenosylcobalamin and methyl cobalamin containing preparations prepared in Example 5 and the adenosylcobalamin and tacrolimus hydrate containing preparations prepared in Example 10. Moreover, a base control without an active ingredient was also prepared by adding base components. Positive control medicine was prepared by 0.1% tacrolimus ointment and 0.1% dexametasone cream.

Preparation of Animal Test Subject with Dermatitis 7-8 week old male nude mice were used as test subjects. 5% sodium dodecyl sulfate (SDS) was treated twice daily for 7 days to damage functions in skin a horny layer, the before value of water retention in Table 3 was measured by using water evaporation measuring device (Tewameter, Germany).

Evaluation of Water Retention

Test preparations, positive control preparations and base control preparations were applied twice daily for 2 days in a dosage of 100 μL per skin area 10 cm². The values of water retention were measured and provided in Table 3.

TABLE 3

| Preparations | No. of subjects | Before | After 1 day | After 2 days | After 3 days | After 4 days |
|---|---|---|---|---|---|---|
| Base control | 3 | 67 ± 2 | 71 ± 1 | 69 ± 3 | 69 ± 1 | 67 ± 2 |
| Positive control (0.1% tacrolimus ointment) | 3 | 68 ± 2 | 85 ± 1 | 83 ± 1 | 80 ± 2 | 75 ± 2 |
| Positive control (0.1% dexametasone cream) | 3 | 70 ± 2 | 88 ± 2 | 85 ± 3 | 79 ± 1 | 74 ± 1 |
| Example 2 | 3 | 68 ± 1 | 87 ± 2 | 85 ± 2 | 80 ± 2 | 78 ± 1 |
| Comp. Ex. 2 | 3 | 67 ± 2 | 75 ± 2 | 79 ± 1 | 78 ± 2 | 76 ± 1 |
| Example 5 | 3 | 71 ± 2 | 88 ± 2 | 84 ± 1 | 83 ± 3 | 81 ± 1 |
| Example 8 | 3 | 68 ± 2 | 88 ± 1 | 86 ± 2 | 80 ± 1 | 79 ± 2 |
| Example 10 | 3 | 69 ± 1 | 87 ± 1 | 85 ± 2 | 81 ± 2 | 80 ± 1 |

As set forth in Table 3, the adenosylcobalamin containing preparations of Example 2 was superior to the cyanocobalamin containing preparations of Comparative Example 2 in retaining water. Preparations further containing skin accelerator in Example 5 showed more superior activity compared to the preparations of Example 2. Multi-component preparations in Example 8 and Example 10 were also superior to single-component preparations in Example 2.

Test Example 3: Toxicity Test of Adenosylcobalamin

For repeated dose toxicity study of adenosylcobalamin (100 mg), 16-hour-fasted 4-5 week old ICR mice (5 mice each group) were selected as test subjects. 100 mg of adenosylcobalamin dissolved in 0.5% carboxymethyl cellulose (CMC) was repeatedly administered by oral route for 5 days. There was neither a dead subject nor abnormal findings such as damages to internal organs.

Formulation Example 1: Preparation of Ointment

Hereunder is provided a description of how to prepare the ointments for external application containing adenosylcobalamin.

Contents (Based on 100 g of Total Formulation)
(a) 0.07 g of adenosylcobalamin;
(b) 1 g of stearic acid, 10 g of monostearic acid, 4 g of monostearic acid poly(oxyethylene glycol), 1.5 g of poly (oxyethylcetostearyl ether) (20 ethylene oxide), 1.2 g of poly(oxyethylcetostearyl ether), 3 g of cetanol and 10 g of liquid paraffin; and
(c) 10 g of 1,3-butylene glycol, 6 g of glycerin and a balance of distilled water Preparation Method The oil phase, i.e. the composition (b), was exactly weighed and placed in a supplemental tank, followed by heating up to 75° C. for dissolution. The water phase, i.e. the composition (c), was exactly weighed and placed in an emulsifying tank, followed by heating up to 75° C. for dissolution and addition of the component (a).

The oil phase was added into the emulsifying tank at vacuum condition, and stirred with a homogenizer (3500 rpm) and a pedal mixer (100 rpm), followed by cooling down to about 25° C. and aging, thus providing ointments for external application.

Formulation Example 2: Preparation of Liquids for External Application

Hereunder is provided a description of how to prepare the liquids for external application containing adenosylcobalamin.

Contents (Based on 100 g of Total Formulation)
0.1 g of adenosylcobalamin, 0.5 g of isopropanol, 0.5 g of cetanol, 0.2 g of 1,3-butylene glycol, 0.5 g of carboxy methyl cellulose and a balance of distilled water.

Preparation Method

Cetanol was exactly weighed and placed in a supplemental Tank, followed by heating up to 70° C. for dissolution. Sodium carboxy methyl cellulose, 1,3-butylene glycol and adenosylcobalamin were moisted in distilled water with stirring, and placed in a main tank, followed by heating up to 70° C. for dissolution. The solution in the supplemental tank was slowly added into the main tank and cooled down to 40° C., followed by addition of isopropanol, and then cooled with stirring by using a pedal mixer at 50 rpm down to about 25° C. and aged, thus providing liquids for external application.

Formulation Example 3: Preparation of Suspensions for External Application

Hereunder is provided a description of how to prepare the suspensions for external application containing adenosylcobalamin and methyl cobalamin.

Contents (Based on 100 g of Total Formulation)
(a) 0.1 g of adenosylcobalamin and 0.05 g of methyl cobalamin;
(b) 1.5 g of stearic acid, 1 g of cetanol, 3 g of white Vaseline, 3 g of squalene, 1.5 g of tri(caprylic acid/capronic acid) glycerin, 1.7 g of monoolefinsorbitan and 4 g of poly(ethylene glycol);
(c) 4 g of dipropylene glycol, 0.5 g of triethanol amine and 50 g of distilled water; and
(d) 8.5 g of isopropanol and balance of distilled water Preparation Method The composition (c) was exactly weighed and placed in a main tank, followed by heating up to 70° C. for dissolution. The composition (b) was exactly weighed and placed in supplemental tank, followed by heating up to 70° C. for dissolution, and then slowly added into the main tank with a homogenizer at 2000 rpm. The composition (c) was added into a main tank, and cooled down to 40° C. with stirring by using pedal mixer at 100 rpm, followed by addition of the composition (d), and then cooled down to 25° C. with stirring by using a pedal mixer at 50 rpm and aged, thus providing suspensions for external application.

Formulation Example 4: Preparation of Plasters

Hereunder is provided a description of how to prepare the plasters for external application containing adenosylcobalamin and tacrolimus hydrate.

Contents (Based on 100 g of Total Formulation)
(a) 2.0 g of adenosylcobalamin and 1 g of tacrolimus hydrate;
(b) 3 g of isopropyl myristate, 5 g of liquid paraffin, 20 g of polybudene and 25 g of 1,3-pentadiene copolymer resin;
(c) 2 g of titanium oxide, 0.1 g of dibutylhydroxytoluene, 1 g of stearic acid polyoxyethylene sorbitan and 2 g of zinc oxide;
(d) 7 g of caoline;
(e) 18 g of solid natural rubber latex and 15 g of solid SBR synthesized rubber; and
(f) 0.07 g of sodium polyacrylate, 1 g of distilled water and 0.5 g of glycerin Preparation Method The composition (b) was exactly weighed and placed in a main tank. The temperature was elevated up to 115° C. for dissolution and maintained at 90° C. After the addition of the composition (a), the temperature was controlled at 70° C. The composition (c) and the composition (d) were admixed in a supplemental Tank, and added into the main tank. Moreover, the composition (f) was added in the main tank, the composition (e) was also added in the main tank at 70° C., thus providing ointments for external application. Thus, the prepared ointments were coated over woven or non-woven fabric (100 g per 1 m$^2$), and such fabric was cut into the dimension of 10 cm×14 cm, consequently providing plasters.

Formulation Example 5: Preparation of Water-Retaining Plasters

Hereunder is provided a description of how to prepare the water-retaining plasters for external application containing adenosylcobalamin and dexametasone propionate.

Contents
(a) 1.0 g of adenosylcobalamin and 0.4 g of dexametason propionate;
(b) 25 g of D-sorbitol, 10 g of distilled water, 15 g of caoline and 1 g of titanium oxide;
(c) 1 g of gelatin and 5 g of distilled water;
(d) 0.2 g of sodium metaphosphate and 1 g of distilled water;
(e) 0.2 g of magnesium hydroxyaluminate, 6 g of sodium polyacrylate, 4 g of propylene glycol, 0.5 g of acrylic acid.starch, 1 g of castor oil, 0.5 g of monoolefinic acid polyoxyethylene sorbitan and 0.5 g of monoolefinic acid sorbitan;
(f) 15 g of D-sorbitol (15 g) and 0.1 g of dibutylhydroxytoluene;
(g) 3 g of methacrylic acid/acrylic acid n-butyl copolymer; and
(h) 5 g of D-sorbitol (5 g) and 1.2 g of tartaric acid Preparation Method The composition (b) was exactly weighed and placed in a main tank, followed by heating up to 40° C. for dissolution.

Moreover, the composition (d) in the supplemental tank, which was heated and dissolved at 40° C., was added in the main tank, and the composition (c) and (g) were also introduced, while mixing the composition in the main tank with a pedal mixer at 100 rpm. After the composition (a) and (e) were admixed and introduced, the composition (h) was slowly added to produce ointments. 12 g of ointments produced thereto were uniformly coated on non-woven fabric in a dimension of 10 cm×14 cm, consequently providing plasters.

Formulation Example 6: Preparation of Skin Lotions

Hereunder is provided a description of how to prepare the skin lotions for external application containing adenosylcobalamin.
Contents (Based on 100 g of Total Formulation)
(a) 0.2 g of adenosylcobalamin;
(b) 0.5 g of sodim carboxymethyl cellulose, 6 g of polyethylene glycol and 4 g of propylene glycol;
(c) 1 g of polyoxyethylene oleincetyl ether and 0.5 g of ojoba oil;
(d) An appropriate amount of perfume and 10 g of ethanol; and
(e) A balance of distilled water
Preparation Method
The composition (e) and (b) were exactly weighed and admixed with each other, and then the mixture was added into a main tank, followed by heating up to 45° C. for dissolution. Further, while stirring the composition in the main tank with a pedal mixer at 100 rpm, the composition (a) was added, dissolved and cooled to the room temperature. The composition (d) was introduced in supplementary tank, and the composition (c) was also added, dispersed, and uniformly stirred with a pedal mixer at 300 rpm.

Formulation Example 7: Preparation of Lotions

Hereunder is provided a description of how to prepare the lotions for external application containing adenosylcobalamin and dexametasone propionate.
Contents (Based on 100 g of Total Formulation)
0.4 g of adenosylcobalamin, 5 g of glycerin, 10 g of isopropanol, 1 g of cetanol, 0.5 g of polyoxyethylene cetostearyl ether, 0.5 g of triethol amine, 3 g of stearic acid and a balance of distilled water
Preparation Method
Cetanol, polyoxyethylene cetostearyl ether, and stearic acid were exactly weighed and added into a main tank, and then stirred with a homogenizer at 2000 rpm, followed by heating up to 70° C. for dissolution. Moreover, triethanol amine, distilled water, adenosylcobalamin and glycerin were added into the supplementary tank and heated up to 70° C. for dissolution while stirring with a pedal mixer at 50 rpm. The composition from the supplementary tank was slowly added into the main tank, and cooled down to 40° C. The composition was abruptly cooled down to 25° C. while adding isopropyl alcohol and stirring continuously, followed by aging, consequently providing lotions.

Test Example 4: Inhibition Test of T-Cell Proliferation

It is typically known that the increase of $CD4^+$ T cells is observed in atopic dermatitis lesion, and cytokines secreted from $CD4^+$ T cells make the condition of atopic dermatitis worse (DirkJan Hijnen et al., J Invest Dermatol 125:1149-1155, 2005). Therefore, we tried to determine the therapeutic effectiveness of cobalamin derivatives for treatment of atopic dermatitis by examining the changes of T-cell proliferation before and after photolysis of cobalamin derivatives.

Mixed lymphocyte reaction (MLR) is a proliferation response mainly caused by the $CD4^+$ T lymphocyte. When the T cell separated from one mouse strain and the dendritic cell (DC, antigen presenting cell) separated from another mouse strain are mixed together, the immune response by the T cell occurs. This immune response is a tissue incompatibility reaction due to the difference of the genes of MHC molecules of the two strains.

In this experiment, the target cell (DC) derived from BALB/C strain and the $CD4^+$ T cell (the responder) derived from C57BL/6 (B6) strain are mixed and co-cultured to induce a 1 way MLR. In this process, several types of cobalamin derivatives (cyanocobalamin, hydroxocobalamin, methylcobalamin, adenosylcobalamin) are treated, and then the intensities of the immune response are measured by comparing the T cell proliferation for each of the cobalamin derivative-treated group.

Preparation of Bone Marrow-Derived Dendritic Cells (BM-DCs)
1) Bone marrow derived dendritic cells were isolated from 8 weeks BALB/c mouse as follows.
2) The femur and tibiae were separated from a mouse, and then soaked in PBS. The muscle tissues were removed from them. Then, the bones were soaked in 70% EtOH for 2 minutes for sterilization, and then EtOH was washed off with PBS.
3) A needle of a 10 ml syringe filled with PBS was inserted into ends of the bones and then PBS was injected into the bones to isolate the bone marrow.
4) The obtained bone marrow was made into a single cell suspension by pipetting.
5) $1 \sim 1.5 \times 10^7$ of leukocytes were isolated per one femur or one tibia.
6) Culture medium was prepared (RPMI-1640+Penicillin/Streptomycin, L-Glutamin, 2-MercaptoEtOH, 10% Fetal Bovine Serum, Recombinant mouse GM-CSF). $2 \times 10^6$ of BM leukocytes were plated onto 100 mm Petri dish with 10 ml of the culture medium. At this time, 200 U/ml (in case of 20 ng/ml, $5 \times 10^6$ U/mg) of rmGM-CSF was added. (Day 0)
7) Day 3, 10 ml of culture medium (including 200 U/ml GM-CSF) was added.
8) Day 6, culture medium replacement: 10 ml of culture medium from the culture plate was taken, and then centrifuged. The obtained cells were released in a fresh medium containing GM-CSF 200 U/ml, and then they were put back into the original culture plate. Through this process, half of the entire culture medium could be changed to a new medium.
9) Day 8, culture medium replacement: Half of the culture medium was replaced in the same way as day 6.
10) Day 9, after collecting BM-DCs by pipetting carefully, and centrifuging at 300 g/RT/5 min, they were poured into 10 ml of fresh culture medium. The BM-DCs were plated on 100 mm tissue culture plate. 100 U/ml of rmGM-CSF and 1 µg/ml of LPS were added to the culture medium. The BM-DCs were fully matured by culturing for an extra day.

B. Preparation of CD4 T Cell (C57BL/6 Mouse)
1) The spleen was separated out from C57BL/6 mouse, and was ground by using the nylon mesh in PBS and then centrifuged at 300×g for 4 min.

2) The obtained cell pellet was treated with 5 ml of ACK RBC lysing solution for 5 minutes in RT, and then washed with PBS.

3) After resuspending the cells in 500 ul of MACs buffer (PBS+EDTA/BSA), the cells were stained with 50 ul of anti-CD4 microbead. Then, the CD4$^+$ T cell ($1\times10^7$ cells) were separated from the cells according to the manual of MACS kit (Miltenyi Company).

C. MLR Response and Analysis

1) The experiment for determining MLR response was designed to comprise control group, photo-exposed group, and photo-nonexposed group as follows. Each group was tested in triplicate according to concentration and substance on 3 wells.

2) Control group was divided into the following three subgroups, i.e., Cyclosporin A-treated group, PBS-treated treatment group (positive control group), no antigen group (no DC-treated, negative control group) and no H3 thymidine group.

① Control Group

TABLE 4

| Subgroup | Concentration |
|---|---|
| Cyclosporin A-treated group | 10, 30, 100 mM |
| PBS-treated treatment group(positive control) | — |
| No antigen group(negative control group) | — |
| No H3 thymidine group | — |

3) Photo-exposed group and photo-nonexposed group are divided to the following subgroups according to the type and the concentration of cobalamin derivative (cyanocobalamin, hydroxocobalamin, methylcobalamin, or adenosylcobalamin) that is treated to the each subgroup. The cobalamin derivatives of the photo-exposed group are exposed under the light for 1 hr before treatment to the cells.

② Photo-Nonexposed Group

TABLE 5

| | Concentration |
|---|---|
| Cyanocobalamin | 10, 30, 100, 500 mM |
| Hydroxocobalamin | 10, 30, 100, 500 mM |
| Methylcobalamin | 10, 30, 100, 500 mM |
| Adenosylcobalamin | 10, 30, 100, 500 mM |

③ Photo-Exposed Group

TABLE 6

| | Concentration |
|---|---|
| Cyanocobalamin | 3, 10, 30, 100 mM |
| Hydroxocobalamin | 3, 10, 30, 100 mM |
| Methylcobalamin | 3, 10, 30, 100 mM |
| Adenosylcobalamin | 3, 10, 30, 100 mM |

4) $1\times10^4$ DC and $2\times10^5$ CD4$^+$ T cells are co-cultured in 96-well round plate for 48 hours (in each 200 μl PRMI1640 culture media/10% FBS) (for all groups except no antigen group (negative control group)). Each cobalamin derivative (cyanocobalamin, hydroxocobalamin, methylcobalamin, adenosylcobalamin) was dissolved in PBS, and treated to be 3 uM~500 uM for photo-exposed group and photo-nonexposed group.

5) After 48 hrs of co-culture, the formation of lymphoblasts transformed from the CD4+ T cells was identified under a microscope. 10μ Ci of H3-thymidine containing a radioactive isotope (H3, tritum) was added to the culture media. The cells were further cultured for an extra 24 hrs in order to permit incorporation of the radioactive isotope in the DNA of the actively replicating T cells. When cell proliferation has progressed, cell division and DNA synthesis occurred. At this time, radioactive thymidine was incorporated in the DNA molecule.

6) The culture media was centrifuged, and then the supernatant was removed. The remaining cell pellet was treated with DW (Distilled Water) to destroy the cell membranes by osmotic pressure shock. In addition, the cells were frozen (−80° C.) and thawed (37° C.) to break the membranes, so that the DNA can get out.

7) The remaining materials in the 96-wells were sucked by using the vacuum-pump harvester machine. In the process, cell debris and DNA fragments of dead cells are discarded through the filter mat, and intact DNA are attached to the filter.

8) The radioactivity values of the filter mat were measured through a beta-counter. (Count Per Min, CPM.) The radioactivity values on the filter mat according to the location of each experimental group were compared to each other. We can judge that the lower the CPM value, the more inhibited the MLR reaction.

9) We compiled the average CPM value of the triplicate experimental groups on a graph. % of inhibition was calculated as follows:

% of inhibition=[CPM (untreated)−CPM (treated)]/ CPM (untreated).

Result

① Control Group

TABLE 7

| Conc. | Group Cyclosporin A | | |
|---|---|---|---|
| 10 μM | 879 | 1112 | 1867 |
| 30 μM | 1524 | 1339 | 1432 |
| 100 μM | 1003 | 601 | 679 |

TABLE 8

| PBS (+ctrl) | | | w/o allogenic DC (−ctrl) | | | no H3 thymidine | | |
|---|---|---|---|---|---|---|---|---|
| 44313 | 50456 | 41293 | 3327 | 2881 | 4115 | 88 | 54 | 60 |
| | 45354 | | | | | | | |

As a result of the experiment for the control group (Tables 7 & 8, and FIG. 1), we could confirm the following:

1) Cyclosporin A-treated group: A strong immunosuppressant, cyclosporine A, inhibited T cell proliferation from 10 uM.

2) PBS-treated treatment group (positive control group): PBS was not valid for inhibition of T cell proliferation. PBS was the buffer used for dissolving the control agent and the experiment substance. PBS was used as the vehicle and was added to confirming it had no effect on this experiment.

3) No antigen group (no DC-treated, negative control group): No antigen group showed little or no T cell proliferation. It did not give any stimulation to the T cell. It was used to confirm that there were no errors in the procedures and techniques during the test. MLR reaction can't occur in this circumstance, because it is not added to the allogenic DC.

4) No H3 thymidine group: No H3 thymidine group had a CPM value of zero, because there was no radioactive substance.

5) Through this conditional test, we could confirm the test system was well-established.

② Photo-Nonexposed Group

TABLE 9

| Conc. | Group | | | | | | | | | | | |
|---|---|---|---|---|---|---|---|---|---|---|---|---|
| | C-co | | | H-co | | | M-co | | | A-co | | |
| 10 μM | 43413 | 39935 | 41240 | 41987 | 33493 | 38243 | 37594 | 43624 | 44951 | 19094 | 19033 | 18047 |
| 30 μM | 42882 | 30722 | 40187 | 33669 | 34862 | 34340 | 36641 | 28896 | 40298 | 14064 | 10071 | 7326 |
| 100 μM | 41663 | 48408 | 39828 | 28541 | 26247 | 29747 | 37066 | 30678 | 39514 | 4603 | 3940 | 2184 |
| 500 μM | 36303 | | 40107 | 14806 | 11254 | 13198 | 22687 | 28924 | 24891 | 1585 | 1141 | 875 |

Figure 2:
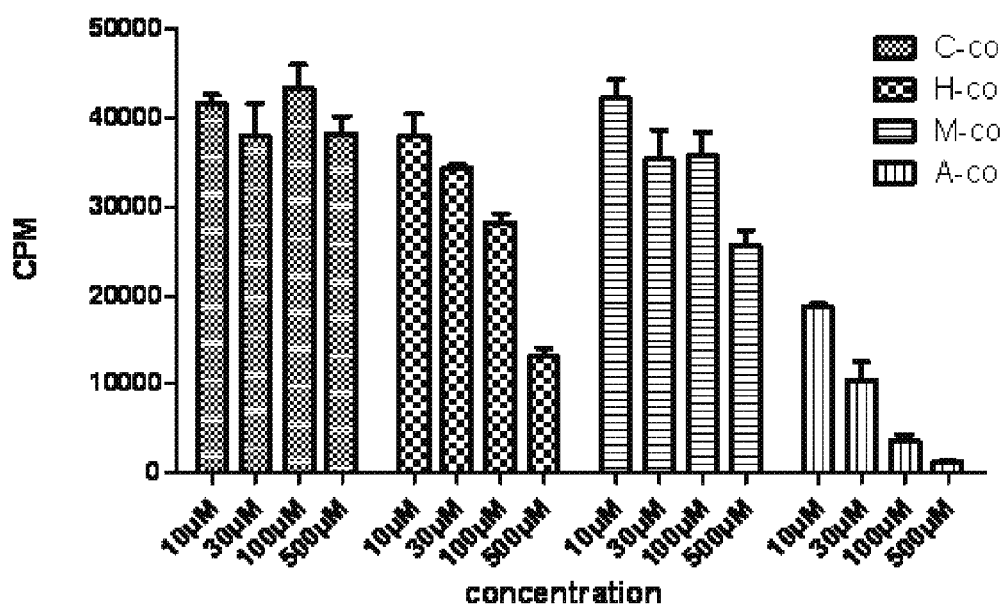

As a result of the experiment for the photo-nonexposed group (Table 9, and FIG. 2), we could confirm the following:

1) Adenosylcobalamin showed the best inhibitory effect on T cell proliferation. hydroxocobalamin was found to inhibit T cell proliferation in concentration-dependent manner, but the effect was not comparable to that of adenosylcobalamin.

2) Especially, at the highest concentration of 500 μM, adenosylcobalamin inhibited T cell proliferation 31.83-folds higher than that of cyanocobalamin. Cyanocobalmin did not inhibit T cell proliferation.

③ Photo-Exposed Group

TABLE 10

| Conc. | Group | | | | | | | | | | | |
|---|---|---|---|---|---|---|---|---|---|---|---|---|
| | Photo-C-co | | | Photo-H-co | | | Photo-M-co | | | Photo-A-co | | |
| 3 μM | 41161 | 57338 | 56253 | 52932 | 46313 | 40358 | 33467 | 32885 | 50368 | 26305 | 14772 | 24306 |
| 10 μM | 39141 | 36381 | 39492 | 42615 | 39452 | 33765 | 42973 | 43693 | 41162 | 2225 | 3123 | 1922 |
| 30 μM | 38702 | 34451 | 34078 | 34824 | 37105 | 32225 | 18844 | 28639 | 29522 | 997 | 1091 | 1391 |
| 100 μM | 50511 | 27692 | 30567 | 37189 | 23765 | 30994 | 8689 | 4599 | 10029 | 696 | 1259 | 1333 |

Figure 3:
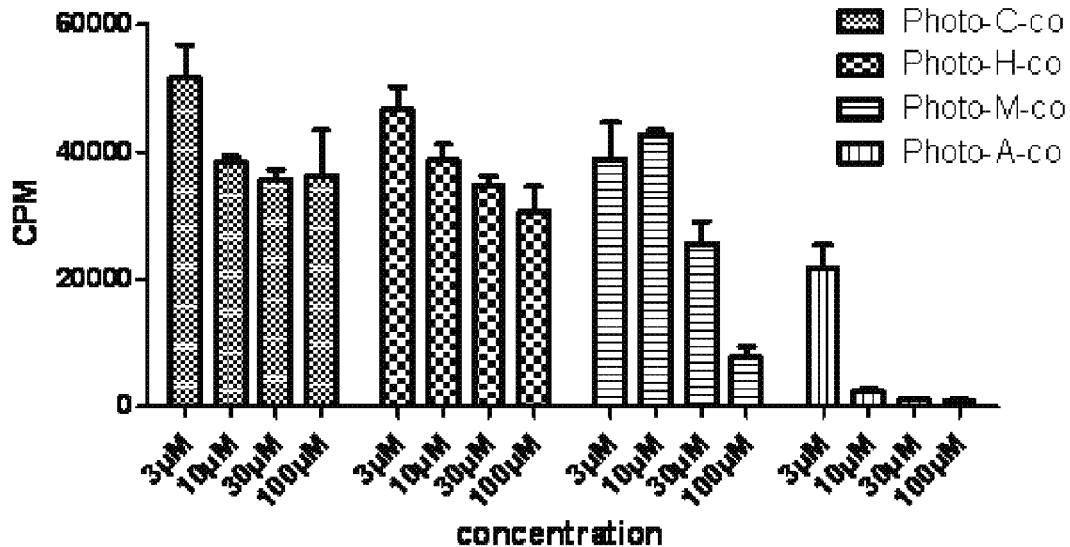

As a result of the experiment for the photo-exposed group (Table 10, and FIG. 3), we could confirm the following:

1) After exposure to light for 1 hour, T cell proliferation was remarkably inhibited by photolyzed adenosylcobalamin. cyanocobalmin and methylcobalamin also inhibited T cell proliferation; however, their effect was not comparable to that of adenosylcobalamin.

2) Especially, at high concentration of 100 μM, adenosylcobalamin inhibited T cell proliferation 33.08-folds higher than cyanocobalamin.

④ Comparison of T Cell Proliferation Inhibition (in %)

Figure 4:
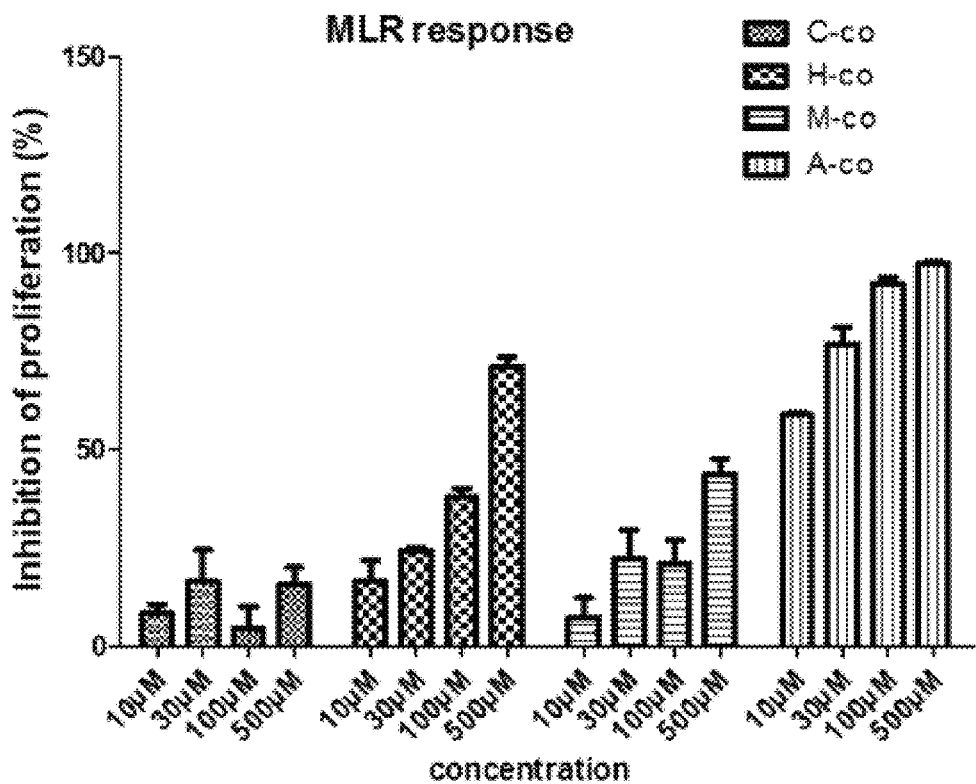
FIG. 4 shows the result of comparison of T cell proliferation inhibition for the Control group, Photo-nonexposed group, and Photo-exposed group.

As a result of comparison of T cell proliferation inhibition (Table 11, and FIG. 4), we could confirm the following:

1) Adenosylcobalamin inhibited T cell proliferation in concentration-dependent manner. It has almost 100% inhibitory effect at the highest concentration. It shows 60% inhibition of the proliferation even at the lowest concentration.

2) But cyanocobalamin shows 25% or less inhibition rate even at the highest concentration.

In comparison with other cobalamins, adenosylcobalamin showed the best inhibitory effect on T cell proliferation. Adenosylcobalamin showed high inhibitory effect in the absence of light, but particularly with exposure to light, T cell proliferation swas inhibited more strongly. Adenosylcobalamin is photolyzed well in light. It shows that adenosylcobalamin produces better effect when it is exposed to the light after applying it on the skin. However, the inhibitory effect of cyanocobalamin on T cell proliferation was almost none existent. Therefore, it can be confirmed that adenosylcobalamin provides a significant therapeutic effect on atopic dermatitis by its strong inhibitory effect on T cell proliferation.

TABLE 11

% of inhibition = [cpm (untreated) − cpm(treated)]/cpm (untreated)

| Conc. | Group | | | | | |
|---|---|---|---|---|---|---|
| | C-co | | | H-co | | |
| 10 μM | 4.279667 | 11.94823 | 9.070865 | 7.423821 | 26.15205 | 15.67888 |
| 30 μM | 5.450456 | 32.26176 | 11.3926 | 25.76399 | 23.13357 | 24.28452 |
| 100 μM | 8.138202 | −6.73369 | 11.96366 | 37.0706 | 42.12859 | 34.41152 |
| 500 μM | 19.95634 | | 11.56899 | 67.35459 | 75.18631 | 70.90003 |

| Conc. | Group | | | | | |
|---|---|---|---|---|---|---|
| | M-co | | | A-co | | |
| 10 μM | 17.10985 | 3.814438 | 0.888566 | 57.90007 | 58.03457 | 60.20858 |
| 30 μM | 19.21109 | 36.28787 | 11.14786 | 68.99061 | 77.79468 | 83.84707 |
| 100 μM | 18.27402 | 32.35878 | 12.87648 | 89.85095 | 91.31278 | 95.18455 |
| 500 μM | 49.97795 | 36.22613 | 45.1184 | 96.50527 | 97.48424 | 98.07073 |

Test Example 5: Cobalamin Type Test

To determine the most effective vitamin B12 derivatives, we examined the effects of various vitamin B12 derivatives (cyanocobalamin, hydroxocobalamin, methylcobalamin, adenosylcobalamin embedded in liposome) on atopic dermatitis mice model.

Test Facility
A. Institution
(1) Name: Korea Research Institute of Chemical Technology
(2) Address: 100 Jang-dong, Yusong-gu, Dejeon, Korea
Materials and Methods
A. Test Material
(1) Name: Adenosylcobalamin, cyanocobalamin, methylcobalamin
(2) Appearance: Scarlet colored gel
(3) Stability: Susceptible to light and temperature
(4) Storage: Keep refrigerated
(5) Routine handling and special precautions: Material is susceptible to light, so it needs to be stored and tested in unlighted condition until it is use in the experiment.
(6) Supplier
Name: Hanall Pharm. Co., Ltd.
Address: Jamsil I-Space $6^{th}$ Floor, Sinchun-dong 11-10, Songpa-gu, Seoul, Korea
(7) Residue treatment: Return after completion of the study
(8) Analysis of the test material:
As agreed upon with the sponsor, stability and homogeneity analysis are not to be carried out separately from the test.
B. Test Material Preparation
(1) 0.7% methylcobalamin embedded in liposome/gel (Group 3)
Gel containing 0.7% methylcobalamin embedded in liposome for external application was prepared as described below under the condition where light was blocked.
① Preparation of Methylcobalamin Embedded in Liposome
Liposomal solution was prepared using thin film hydration method. 4.5 g of 1,2-distearoyl-sn-glycero-phosphocholine (DSPC) and 1.5 g of cholesterol were dissolved in 70.0 mL of chloroform, and then this was followed by vacuum distillation with a rotational evaporation condenser at a temperature above the phase transition temperature (55° C.), thus providing thin lipid membrane on the round-bottomed flask wall. Chloroform remaining in the flask was removed completely through vacuum drying for 24 hours. Hydration was performed by adding 40.0 g of ammonium sulfate solution (250 mM) until the lipid membrane was dispersed completely. After hydration, mono-membrane liposome particles were prepared by passing the solution through a polycarbonate membrane with a pore size of 200 nm for 5 times and a polycarbonate membrane with a pore size of 100 nm for 5 times by using a pressurized extruder. Free ammonium sulfate was removed by using cellulose dialysis tubes for 24 hours at 4° C., and water was added to provide 50.0 g of total solution.

Methylcobalamin solution was prepared by dissolving 2.8 g of methylcobalamin in 50.0 g of water.

Liposomal solution and methylcobalamin solution obtained above were mixed and then incubated for 1 hour at 60° C., thus producing 2.8% methylcobalamin embedded in liposome.

② Preparation of Gel Containing 0.7% Methylcobalamin Embedded in Liposome
(i) Contents (Based on 100.0 g of Total Formulation)

TABLE 12

| Composition Part | Ingredients | Weight (g) |
|---|---|---|
| (a) | Hydroxyethyl cellulose (Natrosol ®) | 0.05 |
|  | Water | 25.4 |
| (b) | EDTA disodium | 0.05 |
|  | Glycerin | 10.0 |
| (c) | 2.0% Carbopol ® 940 aqueous solution | 30.0 |
|  | 10.0% Triethanolamine aqueous solution | 6.0 |
| (d) | Methylparaben | 0.2 |
|  | Ethanol | 3.0 |
| (e) | Polyoxyethylene hydrogenated castor oil 60 (HCO-60 ®) | 0.3 |
| (f) | 2.8% methylcobalamin embedded in liposome | 25.0 |

(ii) Preparation Method
Composition (a) was prepared in a main beaker by dissolving hydroxyethyl cellulose (Natrosol®) in water at 40° C. and then cooling it down to 25° C. Composition (b) was weighed exactly and added into the main beaker with stirring. Composition (c) was prepared by mixing 10.0% triethanolamine aqueous solution with 2.0% Carbopol® 940 aqueous solution in the first supplementary beaker with stirring. Composition (d) was prepared by dissolving methylparaben into ethanol in the second supplementary beaker. Composition (e) was prepared by dissolving polyoxyethylene hydrogenated castor oil 60 (HCO-60®) in the third supplementary beaker at 60° C. Composition (c) was mixed with composition (f) in the first supplementary beaker with stirring. The mixture of composition (c) and (f), composition (d) and composition (e) were added to the main beaker, followed by mixing until the mixture became homogeneous, thus providing a gel containing 0.7% methylcobalamin embedded in liposome.

(2) 0.7% Cyanocobalamin Embedded in Liposome/Gel (Group 4)
Gel containing 0.7% cyanocobalamin embedded in liposome was prepared by the same method of preparing gel containing 0.7% methylcobalamin embedded in liposome in Group 3, except that cyanocobalamin was used instead of methylcobalamin.

(3) 0.7% Adenosylcobalamin Embedded in Liposome/Gel (Group 5)
Gel containing 0.7% adenosylcobalamin embedded in liposome was prepared by the same method of preparing gel containing 0.7% methylcobalamin embedded in liposome in Group 3, except that adenosylcobalamin was used instead of methylcobalamin.

C. Experimental Animals and Environmental Condition
(1) Animals:
① Species (sex), strains: Mouse (male), NC/Nga
② Supplier:
Name: Korea Research Institute of Chemical Technology
Address: Jangdong, 100, Yusung-gu, Daejeon, Korea
③ Producer:
Name: Korea Research Institute of Chemical Technology
Address: Jangdong, 100, Yusung-gu, Daejeon, Korea
④ Justification for species selection: Nc/Nga mouse model is the most common used in inducing atopic dermatitis, and the most suitable experimental animal to evaluate the effect of atopic dermatitis medicine.
⑤ Age, body weight range (at administration): 7 weeks, 25-30 g (6) Method of Numbering Individual Animals:

Weights of the animals were measured and marked on their tails using a permanent marker according to the individual identification method.

(7) Group Assignment:

At the end of quarantine and purification period, healthy mice that had no aberration in weight increase were selected and divided into groups of 4-8.

(8) Animal Identification:

At the end of grouping, each animal was marked on its tail using a permanent marker according to the individual identification method.

(2) Environmental Condition:

| | |
|---|---|
| Temperature | 23 ± 2° C. |
| Relative Humidity | 50 ± 10% |
| Air change | All-in/all-out air system, 10-20 times/hr |
| Lighting | 12 hr of light on/12 hr of light off |
| Intensity of illumination | 150-300 Lux |

(3) Kind of Food, Drinking Water and Delivery Method:

Mice were freely fed with food for experimental animals (Purina Korea Inc.) and with filtered/sterilized water in a polycarbonate bottle.

D. Study Design

Figure 7:
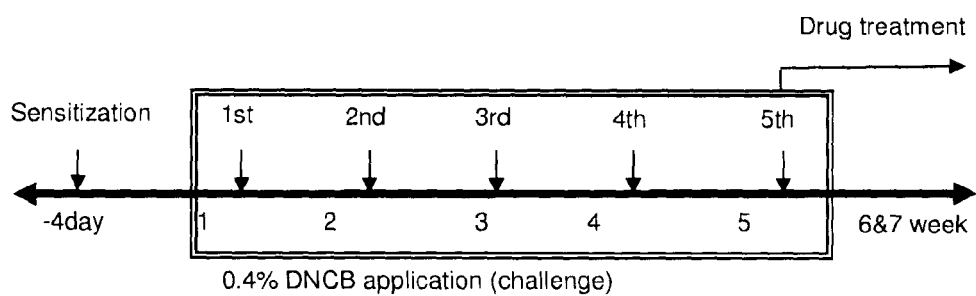
FIG. 7 shows the study design for Cobalamin Type Test of Test Example 5.

FIG. 7 shows the study design for Cobalamin Type Test of Test Example 5.

(1) Sensitization: The hair on the backs of NC/Nga mice were removed from the lower ear region to the upper tail region. Mice were left for 24 hours and then were evenly applied with 1% DNCB solution (Acetone:Olive oil=3:1).

(2) Challenge: At 4 days after sensitization, 0.4% DNCB was applied once a week for 5 weeks to induce skin damage.

E. Group, Dose, Animal Number Per Group, and Administration Route (1) Group

TABLE 13

| Groups | Administered amount (g) | Number of mice |
|---|---|---|
| Normal control (no DNCB treated) | 0 | 4 |
| Negative control (DNCB only) | 0.25 | 8 |
| 0.7% Methylcobalamin embedded in liposome/gel | 0.25 | 8 |
| 0.7% Cyanocobalamin embedded in liposome/gel | 0.25 | 8 |
| 0.7% Adenosylcobalamin embedded in liposome/gel | 0.25 | 8 |

(2) Grouping

All groups except the normal control group, which was not treated with DNCB, were grouped into groups of 8 mice and the normal control was grouped into a group of 4 mice.

(3) Route and Frequency of Administration

After 5 weeks of the first treatment of 0.4% DNCB, 0.4% DNCB was topically applied once a day for 3 weeks.

(4) Method of Treatment

It was applied on the skin using a spatula.

F. Observation and Examination (1) Body Weight Measurement

Every mice of each treatment group was weighed once a week following the drug administration, after 5 weeks of the first treatment of 0.4% DNCB.

(2) Intensity Scoring of Skin Damage

Intensity score of the atopic dermatitis was determined according to SCORAD (Scoring Atopic Dermatitis), based on the following: 0 point for showing no symptoms, 1 point for mild indication of symptoms (mild), 2 points for moderate indication of symptoms (moderate), and 3 points for severe indication of symptoms (severe). Five symptoms considered for scoring were edema, oozing/crusting, excoriation, erythema, and lichenification. The maximum score was 15 points. Intensity scoring of the skin damage was evaluated at 7 weeks after sensitization.

(3) Histological Analysis of Epidermal Tissue

All mice were sacrificed at the end of the experiment. Epidermal tissue was cut out (about 0.5×1.0 cm), fixed in 4% formalin, embedded in paraffin and sliced into 8 μm slides. The tissue slices were adhered to slides, dyed in hematoxylin and eosin and studied under the microscope.

G. Statistical Analysis

All test results were represented as the mean value±standard deviation. When the Levene's tests were carried out and if dispersion indicated homogeneity, student t-tests were conducted to decide statistical significance.

V. Results

A. Changes in Body Weight

There were no groups that showed decrease in body weight after the drug treatment (data not shown).

B. Intensity Scoring of Skin Damage

Table 14 shows of Vit. B12 derivatives on dorsal skin scoring from DNCB-induced atopic dermatitis in NC/Nga mice.

TABLE 14

| | Dorsal skin scoring criteria | | | | | |
|---|---|---|---|---|---|---|
| I.D. | ery-thema | edema/papulation | oozing/crusting | exco-riation | licheni-fication | Total |
| G1-1 | 0 | 0 | 0 | 0 | 0 | 0 |
| G1-2 | 0 | 0 | 0 | 0 | 0 | 0 |
| G1-3 | 0 | 0 | 0 | 0 | 0 | 0 |
| G1-4 | 0 | 0 | 0 | 0 | 0 | 0 |
| Mean | 0.00 | 0.00 | 0.00 | 0.00 | 0.00 | 0.00 |
| S.D. | 0.00 | 0.00 | 0.00 | 0.00 | 0.00 | 0.00 |
| G2-1 | 1 | 1 | 3 | 0 | 1 | 6 |
| G2-2 | 3 | 0.5 | 1 | 1 | 1 | 6.5 |
| G2-3 | 1 | 1 | 1 | 2 | 1 | 6 |
| G2-4 | 2 | 0.5 | 1 | 2 | 1 | 6.5 |
| G2-5 | 2 | 1 | 2 | 1 | 0 | 6 |
| G2-6 | 1.5 | 1 | 1 | 1 | 0 | 4.5 |
| G2-7 | 1.5 | 0.5 | 1 | 0 | 0 | 3 |
| G2-8 | 2.5 | 0.5 | 1 | 1 | 0 | 5 |
| Mean | 1.81 | 0.75 | 1.38 | 1.00 | 0.50 | 5.44 |
| S.D. | 0.70 | 0.27 | 0.74 | 0.76 | 0.53 | 1.21 |
| G3-1 | 2 | 1.5 | 0 | 0.5 | 0 | 4 |
| G3-2 | 1.5 | 0.5 | 0 | 0 | 0 | 2 |
| G3-3 | 1 | 0.5 | 0 | 0 | 0 | 1.5 |
| G3-4 | 1.5 | 0 | 0 | 0.5 | 0 | 2 |
| G3-5 | 2 | 0 | 0 | 0 | 0 | 2 |
| G3-6 | 1.5 | 0 | 0 | 0.5 | 0 | 2 |
| G3-7 | 1 | 0 | 0 | 0 | 0 | 1 |
| G3-8 | 2.5 | 0 | 0 | 0 | 0 | 2.5 |
| Mean | 1.63 | 0.31 | 0.00 | 0.19 | 0.00 | 2.13 |
| S.D. | 0.52 | 0.53 | 0.00 | 0.26 | 0.00 | 0.88 |
| G4-1 | 3 | 0 | 0 | 0.5 | 0 | 3.5 |
| G4-2 | 0.5 | 0 | 0 | 0 | 0 | 0.5 |
| G4-3 | 2 | 0 | 0 | 0 | 0 | 2 |
| G4-4 | 2 | 0 | 0 | 0 | 0 | 2 |
| G4-5 | 2.5 | 0.5 | 0 | 0 | 0 | 3 |
| G4-6 | 1 | 0 | 0 | 0 | 0 | 1 |
| G4-7 | 1 | 0 | 0 | 0 | 0 | 1 |
| Mean | 1.71 | 0.07 | 0.00 | 0.07 | 0.00 | 1.86 |
| S.D. | 0.91 | 0.19 | 0.00 | 0.19 | 0.00 | 1.11 |
| G5-1 | 1.5 | 0.5 | 0 | 0 | 0 | 2 |
| G5-2 | 0.5 | 0.5 | 0 | 0 | 0 | 1 |

TABLE 14-continued

| | Dorsal skin scoring criteria | | | | | |
|---|---|---|---|---|---|---|
| I.D. | ery-thema | edema/papulation | oozing/crusting | exco-riation | licheni-fication | Total |
| G5-3 | 0 | 1 | 0 | 0 | 0 | 1 |
| G5-4 | 2 | 0 | 0 | 1 | 0 | 3 |
| G5-5 | 0.5 | 0 | 0 | 0 | 0 | 0.5 |
| G5-6 | | | | | | |
| G5-7 | 2 | 0 | 0 | 0 | 0 | 2 |
| G5-8 | 1 | 0 | 0 | 1 | 0 | 2 |
| Mean | 1.07 | 0.28 | 0.00 | 0.28 | 0.00 | 1.64 |
| S.D. | 0.79 | 0.39 | 0.00 | 0.49 | 0.00 | 0.85 |

Compared with the normal control group (no DNCB treated), the negative control group (DNCB only) scored; 5.44±1.21. The methylcobalamin (2.13±0.88), cyanocobalamin (1.86±1.11) and adenosylcobalamin (1.64±0.85) treated groups were statistically significantly difference with the negative control group.

C. Histological Analysis of Epidermal Tissue

Figure 5:
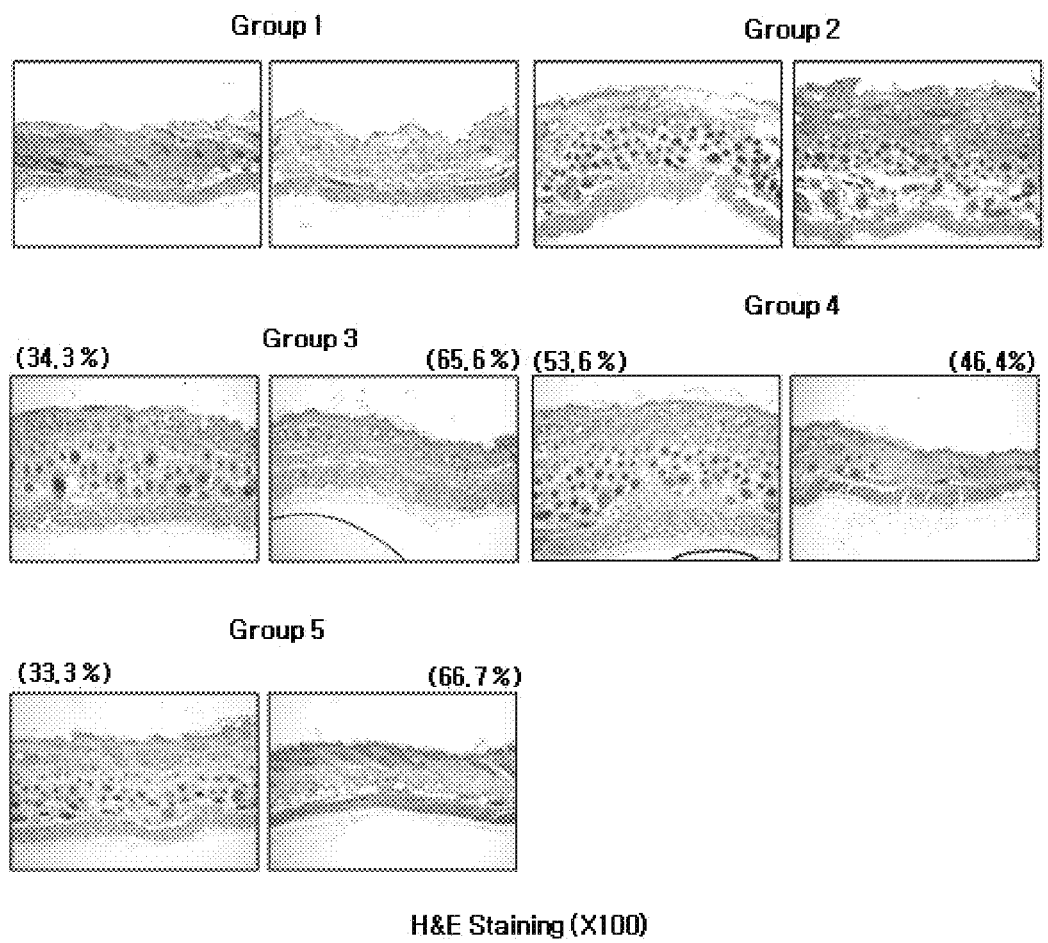
FIG. 5 shows the effects of Vit.B12 derivatives on histology of dorsal skin from DNCB-induced atopic dermatitis in NC/Nga mice according to cobalamin types.

FIG. 5 shows the effects of Vit. B12 derivatives on histology of dorsal skin from DNCB-induced atopic dermatitis in NC/Nga mice.

Compared with the normal control group (no DNCB treated), there were abnormal indications such as infiltration of immune cells and angiogenesis in the negative control group (DNCB only). Abnormal histological features were improved clearly in all tissue sample treated with methyl, cyano and adenosylcobalamin by 65.6%, 46.4% and 66.7%, respectively.

Various derivatives of Vitamin B12 (cobalamin) have been reported to regulate immune reactions. Cyanocobalamin suppresses the cytokine production capacity of T lymphocytes, and methylcobalamin suppresses the synthesis of IL-6 by 60-70% through the action of phytohaemagglutinin or canavalin. Moreover, Vitamin B12 derivatives are reported to control the function of lymphocytes by suppressing the activation of T cells, and to activate and increase the propagation of helper T cells necessary for the synthesis of immunoglobulins in B lymphocytes. This study was designed to find the derivative of Vitamin B12 that demonstrates the highest efficacy in the atopic like skin damage test.

There were no groups that showed rapid decrease in body weight, confirming that there was no toxic effect due to the drug.

The drug treatment for skin damage was effective in all of methylcobalamin (2.1), cyanocobalamin (1.9) and adenosylcobalamin (1.6) treated groups compared to the only DNCB treated group (score-5.4).

When tissue damaged by DNCB was dyed and observed, methyl and adenosylcobalamin treatment showed to be excellent with more than 65% improvement, and cyanocobalamin also showed an improvement of 46%.

In conclusion, it is considered that adenosylcobalamin is the most effective derivative among various Vitamin B12 derivatives in atopic model by the use of DNCB.

Test Example 6: Formulation Type Test

To analyze and compare the efficacy of adenosylcobalamin in different formulations (adenosylcobalamin/cream, adenosylcobalamin/gel, mixture of adenosylcobalamin and empty liposome/gel, and adenosylcobalamin embedded in liposome/gel), different formulations of adenosylcobalamin were applied to atopic dermatitis mouse model.

Test Facility
A. Institution
(1) Name: Korea Research Institute of Chemical Technology
(2) Address: 100 Jang-dong, Yusong-gu, Daejeon, Korea
Materials and Methods
A. Test Material
(1) Name: Adenosylcobalamin
(2) Appearance: Scarlet colored gel
(3) Stability: Susceptible to light and temperature
(4) Storage condition: Keep refrigerated
(5) Routine handling and special precautions: Material is susceptible to light, so it needs to be stored in unlighted condition until it is use in the experiment
(6) Supplier
Name: Hanall Pharm. Co., Ltd.
Address: Jamsil I-Space $6^{th}$ Floor, Sinchun-dong 11-10, Songpa-gu, Seoul, Korea
(7) Residue treatment: Return after completion of the study
(8) Analysis of the Test Material
As agreed upon with the sponsor, stability and homogeneity analysis are not to be carried out separately from the test B. Test Material Preparation
(1) Empty Liposome/Gel (Group 4)
Gel containing empty liposome for external application was prepared as described below under the condition where light was blocked.
① Preparation of Empty Liposomal Solution
Empty liposomal solution was prepared using thin film hydration method. 4.5 g of 1,2-distearoyl-sn-glycero-phosphocholine (DSPC) and 1.5 g of cholesterol were dissolved in 70.0 mL of chloroform, and then this was followed by vacuum distillation with a rotational evaporation condenser at a temperature above the phase transition temperature (55° C.), thus providing thin lipid membrane on the round-bottomed flask wall. Chloroform remaining in the flask was removed completely through vacuum drying for 24 hours. Hydration was performed by adding 90.0 g of water until the lipid membrane was dispersed completely, and water was added to provide 100.0 g of total solution. After hydration, mono-membrane liposome particles were prepared by passing the solution through a polycarbonate membrane with a pore size of 200 nm for 5 times and a polycarbonate membrane with a pore size of 100 nm for 5 times by using a pressurized extruder.
② Preparation of Gel Containing Empty Liposome
(i) Contents (Based on 100.0 g of Total Formulation)

TABLE 15

| Composition Part | Ingredients | Weight (g) |
|---|---|---|
| (a) | Hydroxyethyl cellulose (Natrosol ®) | 0.05 |
| | Water | 25.4 |
| (b) | EDTA disodium | 0.05 |
| | Glycerin | 10.0 |
| (c) | 2.0% Carbopol ® 940 aqueous solution | 30.0 |
| | 10.0% Triethanolamine aqueous solution | 6.0 |
| (d) | Methylparaben | 0.2 |
| | Ethanol | 3.0 |
| (e) | Polyoxyethylene hydrogenated castor oil 60 (HCO-60 ®) | 0.3 |
| (f) | Empty liposomal solution | 25.0 |

(ii) Preparation Method

Composition (a) was prepared in a main beaker by dissolving hydroxyethyl cellulose (Natrosol®) in water at 40° C. and cooling down to 25° C. The composition (b) was exactly weighed and added into the main beaker with stirring. The composition (c) was prepared by mixing 10.0% triethanolamine aqueous solution with 2.0% Carbopol® 940 aqueous solution in the first supplementary beaker with stirring. The composition (d) was prepared by dissolving methylparaben into ethanol in the second supplementary beaker. The composition (e) was prepared by dissolving polyoxyethylene hydrogenated castor oil 60 (HCO-60®) in the third supplementary beaker at 60° C. The composition (c) was mixed with composition (f) in the first supplementary beaker with stirring. The mixture of composition (c) and (f), the composition (d) and the composition (e) were added to the main beaker, followed by mixing until the mixture became homogeneous, thus providing gel containing empty liposome.

(2) 0.7% Adenosylcobalamin/Cream (Group 5)

Cream containing 0.7% adenosylcobalamin for external application was prepared as described below under the condition where light was blocked.

As an aqueous phase, 1.0 g of sodium hydroxide was dissolved in 70.0 g of water and then 0.7 g of adenosylcobalamin was dissolved completely in the solution at 90° C. As an oil phase, 13.0 g of stearic acid, 4.0 g of lanolin, 2.0 g of sucrose esters of fatty acids and 2.0 g of isopropyl myristate were mixed completely at 90° C. The oil phase was added slowly to the aqueous phase at 90° C. while being mixed with a homomixer until the mixture was emulsified homogeneously, followed by adding water to provide 100.0 g of total emulsion. The emulsion was cooled down to 40° C. while being continuously mixed with a homomixer at 3,000 rpm, thus producing emulsified cream. The cream was cooled down to 25° C. and bubbles produced in the cream were removed under vacuum.

(3) 0.7% Adenosylcobalamin/Gel (Group 6)

Gel containing 0.7% adenosylcobalmain for external application was prepared as described below under the condition where light was blocked.

① Preparation of Adenosylcobalamin Solution

Adenosylcobalamin solution was prepared by dissolving 2.8 g of adenosylcobalamin in 90.0 g of water using a mechanical mixer, and water was added to provide 100.0 g of total solution.

② Preparation of Gel Containing 0.7% Adenosylcobalamin

Gel containing 0.7% adenosylcobalamin was prepared by the same method of preparing gel containing empty liposome in Group 4, except that adenosylcobalamin solution was used instead of empty liposomal solution.

(4) Mixture of 0.7% Adenosylcobalamin and Empty Liposome/Gel (Group 7)

Gel containing mixture of 0.7% adenosylcobalamin and empty liposomal solution for external application was prepared as described below under the condition where light was blocked.

① Preparation of Empty Liposomal Solution

Empty liposomal solution was prepared using thin film hydration method. 9.0 g of 1,2-distearoyl-sn-glycero-phosphocholine (DSPC) and 3.0 g of cholesterol were dissolved in 140.0 mL of chloroform, followed by vacuum distillation with a rotational evaporation condenser at a temperature above the phase transition temperature (55° C.), thus providing thin lipid membrane on the round-bottom flask wall. Chloroform remaining in the flask was removed completely through vacuum drying for 24 hours. Hydration was performed by adding 90.0 g of water until the lipid membrane was dispersed completely, and water was added to provide 100.0 g of total solution. After hydration, mono-membrane liposome particles were prepared by passing through a polycarbonate membrane with a pore size of 200 nm for 5 times and a polycarbonate membrane with a pore size of 100 nm for 5 times by using a pressurized extruder.

② Preparation of Adenosylcobalamin Solution

Adenosylcobalamin solution was prepared by dissolving 5.6 g of adenosylcobalamin in 90.0 g of water using a mechanical mixer, and water was added to provide 100.0 g of total solution.

③ Preparation of Gel Containing 0.7% Adenosylcobalamin and Empty Liposome (i) Contents (Based on 100.0 g of Total Formulation)

TABLE 16

| Composition Part | Ingredients | Weight (g) |
|---|---|---|
| (a) | Hydroxyethyl cellulose (Natrosol ®) | 0.05 |
|  | Water | 25.4 |
| (b) | EDTA disodium | 0.05 |
|  | Glycerin | 10.0 |
| (c) | 2.0% Carbopol ® 940 aqueous solution | 30.0 |
|  | 10.0% Triethanolamine aqueous solution | 6.0 |
| (d) | Methylparaben | 0.2 |
|  | Ethanol | 3.0 |
| (e) | Polyoxyethylene hydrogenated castor oil 60 (HCO-60 ®) | 0.3 |
| (f) | Empty liposomal solution | 12.5 |
| (g) | Adenosylcobalamin solution | 12.5 |

(ii) Preparation Method

Composition (a) was prepared in a main beaker by dissolving hydroxyethyl cellulose (Natrosol®) in water at 40° C. and then cooling it down to 25° C. Composition (b) was weighed exactly and added into the main beaker with stirring. Composition (c) was prepared by mixing 10.0% triethanolamine aqueous solution with 2.0% Carbopol® 940 aqueous solution in the first supplementary beaker with stirring. Composition (d) was prepared by dissolving methylparaben into ethanol in the second supplementary beaker. Composition (e) was prepared by dissolving polyoxyethylene hydrogenated castor oil 60 (HCO-60®) in the third supplementary beaker at 60° C. Composition (c) was mixed with composition (f) and (g) in the first supplementary beaker with stirring. The mixture of composition (c), (f) and (g), the composition (d) and the composition (e) were added to the main beaker, followed by mixing until the mixture became homogeneous, thus providing a gel containing 0.7% adenosylcobalamin and empty liposome.

(5) 0.7% Adenosylcobalamin Embedded in Liposome/Gel (Group 8)

Gel containing 0.7% adenosylcobalamin embedded in liposome for external application was prepared as described below under the condition where light was blocked.

① Preparation of Adenosylcobalamin Embedded in Liposome

Liposomal solution was prepared according to thin film hydration method. 4.5 g of 1,2-distearoyl-sn-glycero-phosphocholine (DSPC) and 1.5 g of cholesterol were dissolved in 70.0 mL of chloroform, followed by vacuum distillation with a rotational evaporation condenser at a temperature above the phase transition temperature (55° C.), and thus providing thin lipid membrane on the round-bottomed flask wall. Chloroform remaining in the flask was removed completely through vacuum drying for 24 hours. Hydration was performed by adding 40.0 g of ammonium sulfate solution (250 mM) until the lipid membrane was dispersed completely. After hydration, mono-membrane liposome particles were prepared by passing through a polycarbonate membrane with a pore size of 200 nm for 5 times and a polycarbonate membrane with a pore size of 100 nm for 5 times by using a pressurized extruder. Free ammonium sulfate was removed by using cellulose dialysis tubes for 24 hours at 4° C., and water was added to provide 50.0 g of total solution.

Adenosylcobalamin solution was prepared by dissolving 2.8 g of adenosylcobalamin in 50.0 g of water.

Liposomal solution and adenosylcobalamin solution obtained above were mixed and then incubated for 1 hour at 60° C., thus producing 2.8% adenosylcobalamin embedded in liposome.

② Preparation of Gel Containing 0.7% Adenosylcobalamin Embedded in Liposome

Gel containing 0.7% adenosylcobalamin embedded in liposome was prepared by the same method of preparing gel containing empty liposome in Group 4, except that adenosylcobalamin embedded in liposome was used instead of empty liposomal solution.

C. Animal Systems and Environmental Condition (1) Animals Systems

① Species (sex), strains: Mouse (male), NC/Nga

② Supplier

Name: Korea Research Institute of Chemical Technology

Address: Jangdong, 100, Yusung-gu, Daejeon, Korea

③ Producer

Name: Korea Research Institute of Chemical Technology

Address: Jangdong, 100, Yusung-gu, Daejeon, Korea

④ Justification for Species Selection

NC/Nga mouse is the most common model used in inducing atopic dermatitis, and the most suitable experimental animal to evaluate the effect of atopic dermatitis medicine.

⑤ Age, body weight range (on administration): 7 weeks, 25-30 g

⑥ Method of Numbering Individual Animals:

Weights of the animals were measured and marked on their tails using a permanent marker according to the individual identification method.

⑧ Group Assignment:

At the end of quarantine and purification period, 53 healthy mice that had no aberration in weight increase were selected and divided into groups of 4-7.

⑧ Animal Identification:

At the end of grouping, each animal was marked on its tail using a permanent marker according to individual identification method.

(2) Environmental Condition

| Temperature | 23 ± 2° C. |
|---|---|
| Relative humidity | 50 ± 10% |
| Air change | All-in/all-out air system, 10-20 times/hr |
| Lighting | 12 hr of light on/12 hr of light off |
| Intensity of illumination | 150-300 Lux |

(3) Kind of Food, Drinking Water and Delivery Method

Mice were freely fed with food for experimental animals (Purina Korea Inc.) and with filtered/sterilized water in a polycarbonate bottle.

D. Study Design

Figure 8:
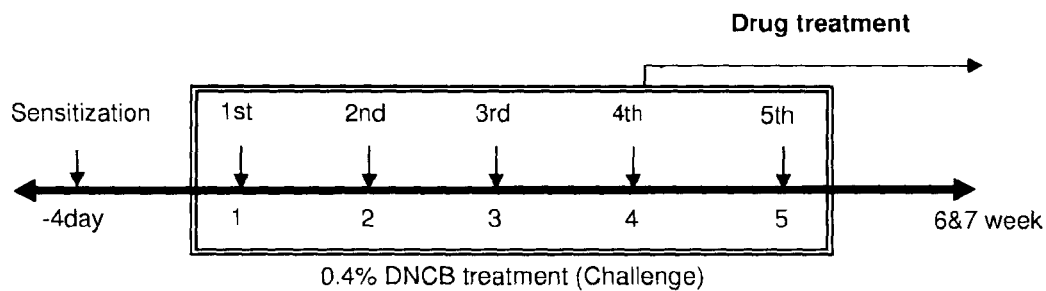
FIG. 8 shows the study design for Formulation Type Test of Test Example 6.

FIG. 8 shows the study design for Formulation Type Test of Test Example 6.

(1) Sensitization: The hair on the backs of NC/Nga mice were removed from the lower ear region to the upper tail region. Mice were left for 24 hours and then were evenly applied with 1% DNCB solution (Acetone:Olive oil=3:1).

(2) Challenge: At 4 days after sensitization, 0.4% DNCB was applied once a week for 5 weeks to induce skin damage.

E. Group, Dose, Animal Number Per Group, and Administration Route (1) Group

TABLE 17

| Groups | Administered amount (g) | Number of mice |
|---|---|---|
| Normal control (no DNCB treated) | 0 | 4 |
| Negative control (DNCB only) | 0.25 | 7 |
| Positive control (Protopic ® 0.1%) | 0.25 | 7 |
| Empty liposome/gel | 0.25 | 7 |
| 0.7% Adenosylcobalamin/gel | 0.25 | 7 |
| 0.7% Adenosylcobalamin/gel | 0.25 | 7 |
| Mixture of 0.7% Adenosylcobalamin and empty liposome/gel | 0.25 | 7 |
| 0.7% Adenosylcobalamin embedded in liposome/gel | 0.25 | 7 |

(2) Grouping

All groups except the normal control group, which was not treated with DNCB, were grouped in groups of 7 mice and the normal control group was grouped in a group of 4 mice.

(3) Route and Frequency of Treatment

After 4 weeks of the first treatment of 0.4% DNCB, 0.4% DNCB was topically applied once a day for 3 weeks.

(4) Method of Treatment

It was applied on the skin using a spatula.

F. Observation and Examination (1) Intensity Scoring of Skin Damage

Intensity score of atopic dermatitis was determined according to the SCORAD (Scoring Atopic Dermatitis), based on the following criteria: 0 point for showing no symptoms, 1 point for mild indication of symptoms (mild), 2 points for moderate symptoms (moderate), and 3 points for severe symptoms (severe). Five symptoms considered for scoring were edema, oozing/crusting, excoriation, erythema, and lichenification. The maximum scoring was 15 points. Intensity scoring of skin damage was evaluated at 7 weeks after sensitization.

(2) Histological Analysis of Epidermal Tissue

All mice were sacrificed at the end of the experiment. Epidermal tissue was cut out (about 0.5×1.0 cm), fixed in 4% formalin, embedded in paraffin and sliced into 8 □m slides. The tissue slices were adhered to slides, dyed in hematoxylin and eosin, and studied under the microscope.

G. Statistical Analysis

All test results were represented as the mean value±standard deviation. When Levene's tests were carried out and if dispersion indicated homogeneity, student t-tests were conducted to decide statistical significance.

Results

A. Intensity Scoring of Skin Damage

TABLE 18

Dorsal skin scoring Intensity criteria

| I.D. | ery-thema | edema/papulation | oozing/crusting | exco-riation | licheni-fication | total |
|---|---|---|---|---|---|---|
| G1-1 | 0 | 0 | 0 | 0 | 0 | 0 |
| G1-2 | 0 | 0 | 0 | 0 | 0 | 0 |
| G1-3 | 0 | 0 | 0 | 0 | 0 | 0 |
| G1-4 | 0 | 0 | 0 | 0 | 0 | 0 |
| Mean | 0.00 | 0.00 | 0.00 | 0.00 | 0.00 | 0.00 |
| S.D. | 0.00 | 0.00 | 0.00 | 0.00 | 0.00 | 0.00 |
| G2-1 | 2 | 2 | 1 | 1 | 0 | 6 |
| G2-2 | 1 | 1 | 1 | 2 | 0 | 5 |
| G2-3 | 1 | 1 | 1 | 1 | 0 | 4 |
| G2-4 | 1 | 1 | 1 | 1 | 0 | 4 |
| G2-5 | 1 | 1 | 2 | 1 | 0 | 5 |
| G2-6 | 0.5 | 1 | 1 | 0 | 1 | 3.5 |
| G2-7 | 1 | 0 | 0 | 0 | 1 | 2 |
| Mean | 1.07 | 1.00 | 1.00 | 0.86 | 0.29 | 4.21 |
| S.D. | 0.45 | 0.58 | 0.58 | 0.69 | 0.49 | 1.29 |
| G3-1 | 0 | 0 | 1 | 0 | 0 | 1 |
| G3-2 | 0.5 | 0 | 2 | 0 | 0 | 2.5 |
| G3-3 | 1 | 0 | 0.5 | 0 | 0 | 1.5 |
| G3-4 | 0 | 0 | 0.5 | 0 | 0 | 0.5 |
| G3-5 | 0.5 | 0 | 0 | 0 | 0 | 0.5 |
| G3-6 | 1 | 0 | 0.5 | 0 | 0 | 1.5 |
| G3-7 | 1.5 | 0 | 0.5 | 0 | 0 | 2 |
| Mean | 0.64 | 0.00 | 0.71 | 0.00 | 0.00 | 1.36 |
| S.D. | 0.56 | 0.00 | 0.64 | 0.00 | 0.00 | 0.75 |
| G4-1 | 2 | 0 | 2 | 1 | 0 | 5 |
| G4-2 | 1.5 | 0 | 1 | 0 | 0 | 2.5 |
| G4-3 | 1.5 | 0 | 2 | 0 | 0 | 3.5 |
| G4-4 | 2 | 0 | 0.5 | 0 | 0 | 2.5 |
| G4-5 | 3 | 0 | 0.5 | 0 | 0 | 3.5 |
| G4-6 | 2 | 0 | 2 | 1 | 0 | 5 |
| G4-7 | 2 | 0 | 1 | 0 | 0 | 3 |
| Mean | 2.00 | 0.00 | 1.29 | 0.29 | 0.00 | 3.57 |
| S.D. | 0.50 | 0.00 | 0.70 | 0.49 | 0.00 | 1.06 |
| G5-1 | 0 | 2 | 1 | 0 | 0 | 3 |
| G5-2 | 0 | 2 | 1 | 1 | 0 | 4 |
| G5-3 | 0 | 2 | 1 | 1 | 0 | 4 |
| G2-4 | 1 | 0 | 0.5 | 0 | 0 | 1.5 |
| G2-5 | 0 | 1.5 | 1 | 1.5 | 0 | 4 |
| G5-6 | 0 | 1 | 0 | 0 | 0 | 1 |
| G5-7 | 0 | 0 | 1 | 1 | 0 | 2 |
| Mean | 0.14 | 1.21 | 0.79 | 0.64 | 0.00 | 2.79 |
| S.D. | 0.38 | 0.91 | 0.39 | 0.63 | 0.00 | 1.29 |
| G6-1 | 3 | 0 | 1 | 0 | 0 | 4 |
| G6-2 | 3 | 0 | 1 | 0 | 0 | 4 |
| G6-3 | 3 | 0 | 2 | 0 | 0 | 5 |
| G6-4 | 3 | 0 | 1 | 0 | 0 | 4 |
| G6-5 | 3 | 1 | 1.5 | 0 | 0 | 5.5 |
| G6-6 | 3 | 0 | 2 | 0 | 0 | 5 |
| G6-7 | 3 | 0 | 2 | 0 | 0 | 5 |
| Mean | 3.00 | 0.14 | 1.50 | 0.00 | 0.00 | 4.64 |
| S.D. | 0.00 | 0.38 | 0.50 | 0.00 | 0.00 | 0.63 |
| G7-1 | 1 | 2 | 0 | 0 | 0 | 3 |
| G7-2 | 1 | 1 | 1 | 0 | 0 | 3 |
| G7-3 | 2 | 0 | 1 | 0 | 0 | 3 |
| G7-4 | 1 | 1 | 0 | 1 | 0 | 3 |
| G7-5 | 2 | 1 | 0 | 1 | 0 | 4 |
| G7-6 | 1 | 1.5 | 1 | 0 | 0 | 3.5 |
| G7-7 | 1 | 0 | 0 | 2 | 0 | 3 |
| Mean | 1.29 | 0.93 | 0.43 | 0.57 | 0.00 | 3.21 |
| S.D. | 0.49 | 0.73 | 0.53 | 0.79 | 0.00 | 0.39 |
| G8-1 | 1.5 | 0.5 | 0 | 0 | 0 | 2 |
| G8-2 | 0.5 | 0.5 | 0 | 0 | 0 | 1 |
| G8-3 | 0 | 1 | 0 | 0 | 0 | 1 |
| G8-4 | 2 | 0 | 0 | 1 | 0 | 3 |
| G8-5 | 1 | 0 | 0 | 0 | 0 | 1 |
| G8-6 | 0 | 0 | 0 | 0 | 0 | 0 |
| G8-7 | 2 | 0 | 0 | 0 | 0 | 2 |
| Mean | 1.00 | 0.29 | 0.00 | 0.14 | 0.00 | 1.43 |
| S.D. | 0.87 | 0.39 | 0.00 | 0.38 | 0.00 | 0.98 |

Compared with the normal control group (no DNCB treated), the negative control group (DNCB only) scored 4.21±1.29 for skin damage, confirming that damage was induced by DNCB. The liposome only treated group scored 3.57±1.05, showing no statistically significant difference with the negative control group.

Damage score for groups treated with adenosylcobalamin/cream and mixture of adenosylcobalamin and empty liposome mixture were 2.79±1.29 and 3.21±0.39, respectively, indicating a trend of reduction, but the differences were not statistically significant.

Compared with the negative control group, the adenosylcobalamin/gel group scored higher, 4.64±0.63, whereas the adenosylcobalamin embedded in liposome treated group had a 66% lower score of 1.43±0.98, indicating a potent therapeutic effect.

The positive control (Protopic®) treated group, which served as a positive control, had a value of 1.36±0.75 or 67% improvement, indicating that it was the most effective.

B. Histological Analysis of Epidermal Tissue

Figure 6:
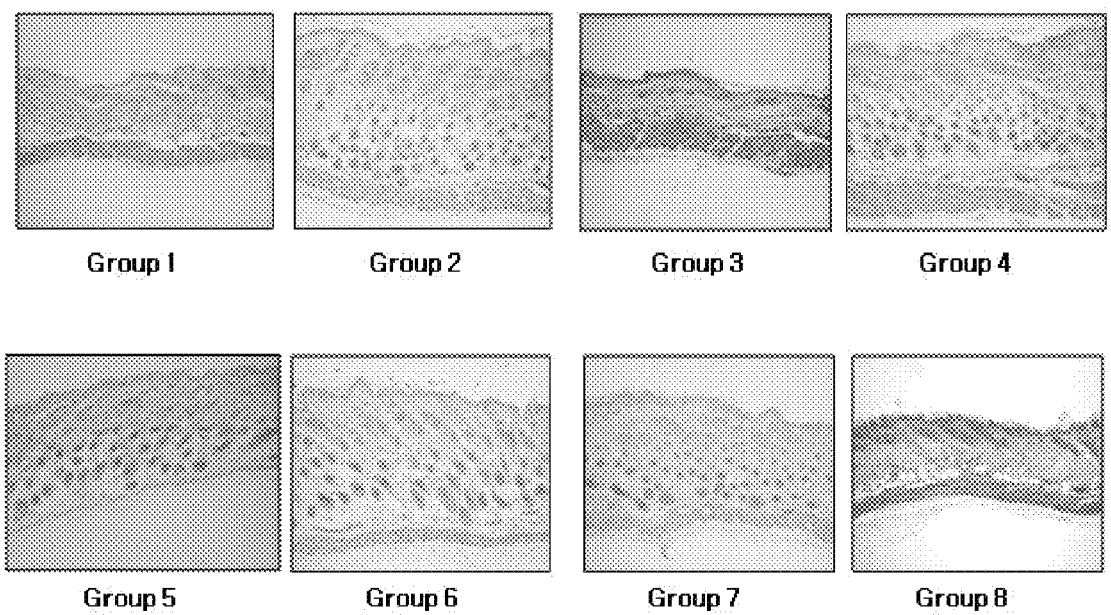
FIG. 6 shows the effects of Vit.B12 derivatives on histology of dorsal skin from DNCB-induced atopic dermatitis in NC/Nga mice according to formulation types.

FIG. 6 shows the effects of Vit.B12 on histology of dorsal skin from DNCB-induced atopic dermatitis in NC/Nga mice.

Histological observation revealed that the thickness of the epidermis and dermis became thicker with DNCB; especially, the tissue structure of the dermis was observed to be loose like that of a sponge. In contrast, the histology of the epidermal tissue was improved considerably when treated with adenosylcobalamin embedded in liposome.

Liposomes discovered by A. Bangham 30 years ago have since been widely used in the fields of biology, biochemistry and medicine. Liposomes are artificial vesicles of the smallest round that have been reported being applied in the delivery of drugs. In the present study, we evaluated the efficacy of adenosylcobalamin for the treatment of atopic dermatitis. In the atopic dermatitis mouse model, we compared the effects of adenosylcobalamin contained in liposome formulation with the cream type, the most common form of drug delivery for skin diseases.

Formulations of adenosylcobalamin/cream, empty liposome/gel or mixture of adenosylcobalamin and empty liposome did not improve the exterior skin condition. Only adenosylcobalamin embedded in liposome treated group was found to improve the DNCB induced atopic like skin damage by approximately 65%.

Histological observation revealed that the epidermis and dermis layer became thickened by DNCB; especially, the tissue structure of the dermis was observed to be loose like that of a sponge. In contrast, the thickness and histological features of the epidermal tissue was improved considerably when treated with adenosylcobalamin embedded in liposome formulation.

In conclusion, adenosylcobalamin embedded in liposome formulation can significantly enhance the drug effects in various parameters (scoring, histological analysis) compared with the adenosylcobalamin/cream formulation.

As set forth above, a composition comprising adenosylcobalamin as an active ingredient according to the present invention was ascertained to effectively suppress edema and rubefaction in the animal test subjects with dermatitis and to increase the skin penetration by comprising a skin accelerator, thus enabling the usefulness of the composition for external application for treating atopic dermatitis.

What is claimed is:

1. A method of treating atopic dermatitis comprising applying to a skin of a subject in need of such treatment an effective amount of an external composition comprising adenosylcobalamin as an active ingredient, wherein the adenosylcobalamin is embedded in a liposome comprising a phospholipid and cholesterol, and the composition comprises 0.01-7 wt % of adenosylcobalamin based on the total weight of the composition.

2. The method of claim 1, wherein the composition further comprises an active ingredient selected from the group consisting of methylcobalamin, hydroxocobalamin, cyanocobalamin, and mixtures a mixture thereof.

3. The method of claim 1, wherein the composition further comprises a steroid, vitamin or immunosuppressive drug.

4. The method of claim 1, wherein the weight ratio of the phospholipid and the cholesterol is 1-10:1.

5. The method of claim 1, wherein the phospholipid is a phosphocholine having 3-24 carbons in diacyl group.

6. The method of claim 5, wherein the phospholipid is selected from the group consisting of 1,2-dipalmitoyl-sn-glycero-3-phosphocholine, 1,2-disteroyl-snglycero-3-phosphocholine, L-a-phosphatidyl choline, 1-palmitoyl-2-glutaroyl-sn-glycero-3-phosphocholine, 1,2-dilauroyl-sn-glycero-3-phosphocholine, 1,2-dimyristoyl-sn-glycero-3-phosphocholine, 1,2-dioleyl-sn-glycero-3-phosphocholine and mixtures a mixture thereof.

7. The method of claim 1, wherein the composition comprises 50-500 weight parts of a surfactant with a C8-C16 alkyl group relative to one weight part of the active ingredient.

8. The method of claim 7, wherein the surfactant is a lauryl ether based compound or poly(ethylene oxide) based compound.

9. The method of claim 8, wherein the lauryl ether based compound is one selected from the group consisting of isopropyl myristate, sodium lauryl sulfate, propylene glycol monolaurate, monolaurin, monostearin, monoolein, monomyristin, lauryl alcohol, polyoxyethylene lauryl ether and mixtures a mixture thereof.

10. The method of claim 8, wherein the poly(ethylene oxide) based compound is one selected from the group consisting of pluronic, sorbitan monopalmitate, sorbitan trioleate, and mixtures a mixture thereof.

11. The method of claim 1, wherein the composition is formulated into a preparation selected from the group consisting of a hydrogel, emulsion cream, ointment, solution, suspension, plaster, water containing plaster, skin lotion and lotion.

12. The method of claim 11, wherein the composition is formulated into the hydrogel.

13. A composition for external application for the treatment of skin diseases, the composition comprising adenosylcobalamin as an active ingredient which wherein the adenosylcobalamin is embedded in a liposome comprising a phospholipid and cholesterol.

* * * * *